US011638784B2

(12) United States Patent
Jones

(10) Patent No.: US 11,638,784 B2
(45) Date of Patent: May 2, 2023

(54) RATCHET MECHANISM AND INJECTION DEVICE

(71) Applicant: SANOFI, Paris (FR)

(72) Inventor: Matthew Meredith Jones, Warwickshire (GB)

(73) Assignee: Sanofi, Paris (FR)

(*) Notice: Subject to any disclaimer, the term of this patent is extended or adjusted under 35 U.S.C. 154(b) by 161 days.

(21) Appl. No.: 16/977,941

(22) PCT Filed: Mar. 11, 2019

(86) PCT No.: PCT/EP2019/055949
§ 371 (c)(1),
(2) Date: Sep. 3, 2020

(87) PCT Pub. No.: WO2019/175073
PCT Pub. Date: Sep. 19, 2019

(65) Prior Publication Data
US 2021/0069422 A1 Mar. 11, 2021

(30) Foreign Application Priority Data

Mar. 13, 2018 (EP) ..................... 18305262

(51) Int. Cl.
A61M 5/315 (2006.01)

(52) U.S. Cl.
CPC .... A61M 5/31526 (2013.01); A61M 5/31551 (2013.01); A61M 5/31585 (2013.01); A61M 2205/581 (2013.01); A61M 2205/582 (2013.01)

(58) Field of Classification Search
CPC .......... A61M 5/31526; A61M 5/31551; A61M 5/31585; A61M 2205/581; A61M 2205/582
See application file for complete search history.

(56) References Cited

U.S. PATENT DOCUMENTS

| 2012/0095410 | A1 | 4/2012 | Moeller et al. | |
| 2014/0088515 | A1* | 3/2014 | Karlsson | A61M 5/20 604/209 |
| 2019/0204578 | A1 | 7/2019 | Fahbach | |

FOREIGN PATENT DOCUMENTS

| WO | WO 2016/193343 | 12/2016 |
| WO | WO 2018/041899 | 3/2018 |
| WO | WO 2018/041988 | 3/2018 |

OTHER PUBLICATIONS

PCT International Preliminary Report on Patentability in International Appln. No. PCT/EP2019/055949, dated Sep. 15, 2020, 8 pages.

(Continued)

Primary Examiner — Dung T Ulsh
(74) Attorney, Agent, or Firm — Fish & Richardson P.C.

(57) ABSTRACT

The present disclosure relates to a ratchet mechanism and to an injection device for expelling of a number of preset or user-selectable doses of a medicament. The ratchet mechanism comprises a housing and a ratchet member that is circularly shaped and rotationally supported relative to the housing. The ratchet member comprises a ratchet surface, a plurality of ratchet features on the ratchet surface, and one or more intermediate ratchet sections on the ratchet surface extending between the plurality of ratchet features. The ratchet mechanism further comprises a counter ratchet member that is circularly shaped, coaxially arranged relative to the ratchet member, rotatable relative to the ratchet member at least along a first sense of rotation, and rotationally supported relative to the housing. The counter ratchet member comprises a counter ratchet surface, a plurality of counter ratchet features on the counter ratchet surface, and one or more intermediate counter ratchet sections.

20 Claims, 11 Drawing Sheets

(56) References Cited

OTHER PUBLICATIONS

PCT International Search Report and Written Opinion in International Appln. No. PCT/EP2019/055949, dated Apr. 16, 2019, 10 pages.

* cited by examiner

Figure 21
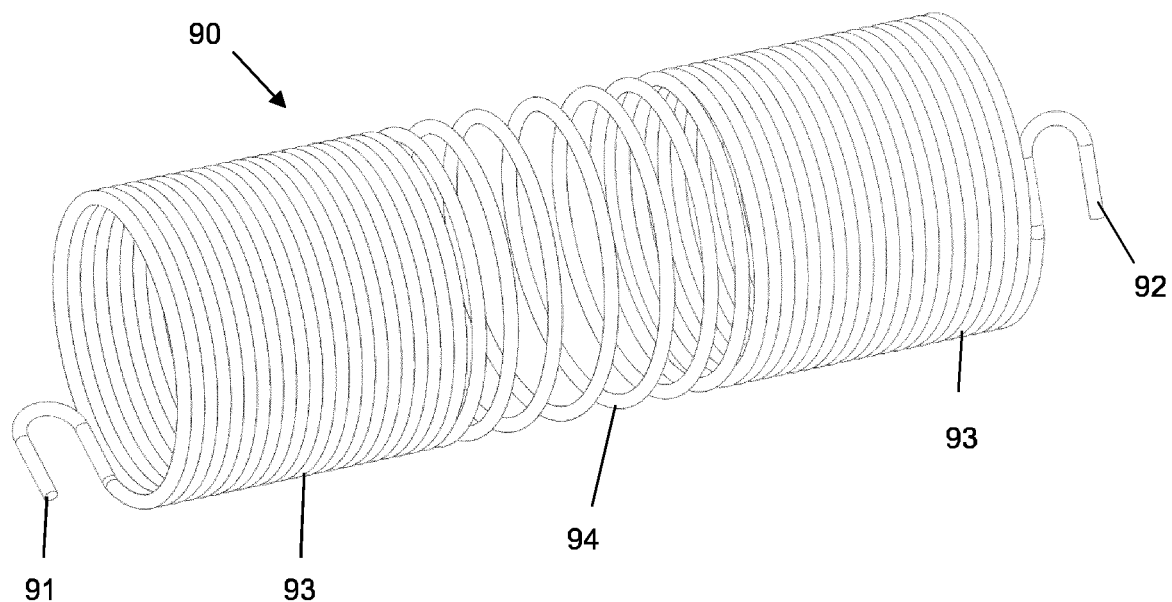
Figure 22a   Figure 22b   Figure 22c
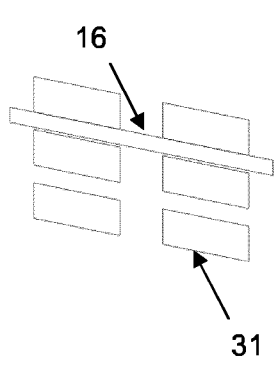
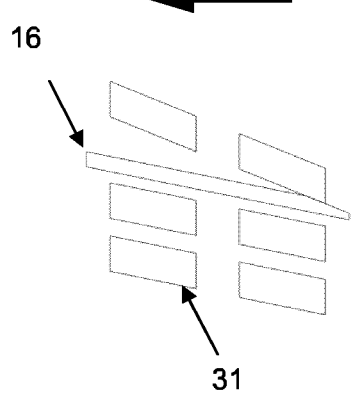
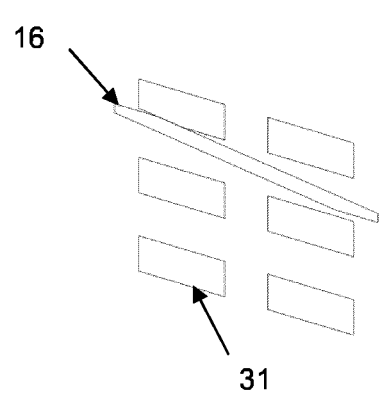

RATCHET MECHANISM AND INJECTION DEVICE

CROSS REFERENCE TO RELATED APPLICATIONS

The present application is the national stage entry of International Patent Application No. PCT/EP2019/055949, filed on Mar. 11, 2019, and claims priority to Application No. EP 18305262.0, filed on Mar. 13, 2018, the disclosures of which are incorporated herein by reference.

TECHNICAL FIELD

The present disclosure relates in one aspect to a ratchet mechanism for an injection device, such like a pen-type injector for expelling of preset or user-selectable doses of a medicament. In particular, the disclosure relates to an injection device comprising an expelling mechanism, such as a windup expelling mechanism and comprising a dose setting mechanism, wherein the ratchet mechanism is configured to reduce and to limit an amount of user-selectable doses to be set and expelled by the injection device.

BACKGROUND

Injection devices for setting and dispensing a single or multiple doses of a liquid medicament are as such well-known in the art. Generally, such devices have substantially a similar purpose as that of an ordinary syringe.

Injection devices, in particular pen-type injectors have to meet a number of user-specific requirements. For instance, with patient's suffering chronic diseases, such like diabetes, the patient may be physically infirm and may also have impaired vision. Suitable injection devices especially intended for home medication therefore need to be robust in construction and should be easy to use. Furthermore, manipulation and general handling of the device and its components should be intelligible and easily understandable. Moreover, a dose setting as well as a dose dispensing procedure must be easy to operate and has to be unambiguous.

Typically, such devices comprise a housing including a particular cartridge holder, adapted to receive a cartridge at least partially filled with the medicament to be dispensed. Such devices further comprise a drive mechanism or expelling mechanism, usually having a displaceable piston rod which is configured to operably engage with a piston of the cartridge. By means of the drive mechanism and its piston rod, the piston of the cartridge is displaceable in a distal direction or dispensing direction and may therefore expel a predefined amount of the medicament via a piercing assembly, which is to be releasably coupled with a distal end section of the housing of the injection device.

The medicament to be dispensed by the injection device is provided and contained in a multi-dose cartridge. Such cartridges typically comprise a vitreous barrel sealed in a distal direction by means of a pierceable seal and being further sealed in proximal direction by the piston. With reusable injection devices an empty cartridge is replaceable by a new one. In contrast to that, injection devices of disposable type are to be discarded when the medicament in the cartridge has been dispensed or used-up.

For some applications it can be advantageous to limit the minimum medicament dose that can be delivered from a device as well as the maximum dose. This may, for example, ensure that only a therapeutically effective dose can be administered. Such a functionality may be particularly relevant to a combinations of drugs, where a minimum quantity of the combined drug is required to ensure sufficient delivery of one element of the combination to be therapeutically effective, whilst allowing some variation of the dose, which may be important for the other element of the combination.

In some applications it may be advantageous to offer a device which allows delivery of only one fixed dose value or a multiple thereof. It may be desirable to offer a device that allows delivery of a minimum fixed dose value and integer multiples of the minimum fixed dose value.

A further application could be for a therapy in which a range of discrete, non-sequential doses of a medication may be required. For example the range of doses may be needed to satisfy the therapeutic needs of different user groups, or to allow individual users to deliver a different dose at different times of the day e.g. in the morning or in the evening.

It is therefore desirable to have an injection device that provides a limitation of deliverable dose values to a limited number of generally available dose values. The injection device should allow a user-defined induced setting and delivery of only one or several fixed dose values. The injection device should be configured to prevent setting or expelling of doses that do not match with a pre-described or predefined dose size.

SUMMARY

In one aspect the disclosure relates to a ratchet mechanism of an injection device or configured for implementation into an injection device. The ratchet mechanism comprises a housing and a circular-shaped ratchet member. The housing may coincide with or may be integrally formed with a housing of the injection device. Typically, the ratchet member is rotationally supported relative to the housing. It may be rotationally supported by the housing and may be located inside the housing.

The ratchet member comprises a ratchet surface and a number of ratchet features located on the ratchet surface or protruding from the ratchet surface. The ratchet member further comprises a number of intermediate sections on the ratchet surface extending between or located between the ratchet features.

The ratchet mechanism further comprises a circular-shaped counter ratchet member. The counter ratchet member may be rotationally supported relative to the housing. It may be rotationally supported by the housing and may be located inside the housing.

The counter ratchet member is coaxially arranged to the ratchet member and is rotatable relative to the ratchet member at least along a first sense of rotation. The counter ratchet member comprises a counter ratchet surface and a number of counter ratchet features located on or protruding from the counter ratchet surface. The counter ratchet member further comprises a number of intermediate sections on the counter ratchet surface extending between or located between the counter ratchet features.

Typically, the intermediate sections between the ratchet features or between the counter ratchet features provide a well-defined spatial separation of adjacently located ratchet features or counter ratchet features, respectively. In other words, the intermediate sections are located adjacent to the ratchet features or counter ratchet features on the ratchet surface or on the counter ratchet surface, respectively. The numerous ratchet features of a ratchet surface and/or the numerous counter ratchet features of the counter ratchet surface are separated from each other by the intermediate sections defining a non-zero distance between adjacently located ratchet features or counter ratchet features.

Rotating of the ratchet member relative to the counter ratchet member along the first sense of rotation requires application of at least a first torque between the ratchet member and the counter ratchet member when at least one of the ratchet features is in engagement with at least one of the counter ratchet features. Application of a torque less than the first torque will be insufficient to overcome or to overhaul the engagement between the at least one ratchet feature with the at least one counter ratchet feature. As long as a torque applied to the ratchet feature along the first sense of rotation is less than the first torque the at least one ratchet member and the at least one counter ratchet member remain engaged thus preventing and impeding a rotation of the ratchet member along the first sense of rotation relative to the counter ratchet member.

Moreover, application of at least a second torque smaller than the first torque between the ratchet member and the counter ratchet member will be sufficient to rotate the ratchet member relative to the counter ratchet member along the first sense of rotation when each of the ratchet features is out of engagement from any of the counter ratchet features. In this situation the at least one ratchet feature may be in engagement with an intermediate section of the counter ratchet surface. Additionally or alternatively the at least one counter ratchet feature may be in engagement with an intermediate section of the ratchet surface.

In this way, the ratchet mechanism provides a multiple torque engagement between the ratchet member and the counter ratchet member. The ratchet mechanism defines at least one angular or rotational position of the ratchet member relative to the counter ratchet member in which a further rotation of the ratchet member along the first sense of rotation relative to the counter ratchet member is effectively blocked because the at least one ratchet feature is mechanically engaged with the at least one counter ratchet feature. In other rotational positions or orientations of the ratchet member relative to the counter ratchet member a torque for rotating the ratchet member relative to the counter ratchet member is comparatively small and is hence supported by the ratchet mechanism.

Specifically, the ratchet mechanism may implemented in a dose setting mechanism or dose expelling mechanism of an injection device, such as a pen-type injection device. The rotational position or orientation of the ratchet member in which the at least one ratchet feature thereof is in mechanical engagement with the at least one counter ratchet feature may correspond to a size of a dose to be set and dispensed by the injection device.

In one example the ratchet feature may be rotatable along a second sense of rotation, opposite to the first sense of rotation under the action of a mechanical energy storage. The rotational state or orientation of the ratchet feature relative to the housing or relative to the counter ratchet feature may correspond to a size of a dose to be set and to be dispensed by a dose expelling mechanism. For setting of a dose the ratchet feature may be rotatable along the second sense of rotation against the action of the mechanical energy storage. The mechanical energy storage may be configured to apply a driving torque to the ratchet member, which driving torque is larger than the second torque. The driving torque is typically smaller than the first torque. Consequently and at the end of a user conducted dose setting procedure the mechanical energy storage serves to rotate the ratchet member along the first sense of rotation, hence along a dose decrementing direction at least until the at least one ratchet feature engages with the at least one counter ratchet feature.

The position, the size and the number of ratchet features and correspondingly shaped counter ratchet features therefore governs the number and the size of specific doses to be set and dispensed by the injection device.

Typically, the ratchet member is rotatable relative to the housing along a second sense of rotation for setting of a dose. It may be rotatable along a first sense of rotation during or for expelling of a dose. The counter ratchet member may be rotationally fixed relative to the housing during and for setting of a dose. The counter ratchet member may be configured to rotate along the first sense of rotation relative to the housing during and for expelling of a dose. A driving torque for rotating the counter ratchet member along the first sense of rotation may be provided entirely by the ratchet member. Insofar, the mutually corresponding ratchet features and counter ratchet features may be configured to provide a transmission of a torque from the ratchet member to the counter ratchet member at least along the first sense of rotation for expelling of a dose of the medicament.

Typically, the ratchet feature is rotatable into numerous discrete rotational positions or rotational orientations relative to the counter ratchet member and/or relative to the housing. In some of these discrete rotational states none of the ratchet features will be in mechanical engagement with any one of the counter ratchet features. Consequently, the rotational state of the ratchet member is unstable. The ratchet member may therefore be subject to a rotation relative to the counter ratchet member until the at least one ratchet feature engages with the at least one counter ratchet feature.

In this way, only in one or in a few of numerous discrete rotational states the ratchet member is in torque proof engagement with the counter ratchet member thus defining at least one dose size of numerous generally available dose sizes governed by the rotational state of the ratchet member relative to the housing or relative to the counter ratchet member. As long as the ratchet member and the counter ratchet member are in an unstable state, e.g. as long as each one of the ratchet features is out of engagement from any of the counter ratchet features a switching of the injection device from a dose setting mode into a dose dispensing or dose expelling mode may be blocked and impeded.

In typical examples the circumferential extension of the intermediate sections of the ratchet surface or of the counter ratchet surface is larger than a circumferential extension of the at least one ratchet member or counter ratchet member. In other embodiments the total circumferential extension of the sum of all intermediate sections is larger than the total circumferential extension of the sum of all ratchet features or counter ratchet features.

Typically, there may be only one, two, three, four, five or six ratchet features or counter ratchet features on the ratchet surface or counter ratchet surface, respectively. In situations, wherein the ratchet feature or counter ratchet feature is rotatable relative to the other one of the ratchet feature or counter ratchet feature in accordance to numerous discrete steps, e.g. in accordance to 10 steps, 20 steps, 24 steps or 30 steps there may be provided a distinct number of ratchet features or counter ratchet features, e.g. two, three, four, five or six ratchet features or counter ratchet features. In this way and in view of a full revolution of the ratchet feature relative to the counter ratchet feature there may be provided only one, two, three, four, five or six discrete angular positions or orientations of the ratchet member relative to the counter ratchet member in which the at least one ratchet feature is in engagement with the at least one counter ratchet feature.

It is generally conceivable, that the ratchet surface comprises only one ratchet feature and that the residual portion of the ratchet surface is provided with the intermediate section. In this way the intermediate section may extend from one side of the ratchet feature to an opposite side of the ratchet feature and may extend all along the ratchet surface. The same may also be valid for the counter ratchet feature. In principle, the counter ratchet feature may comprise only one counter ratchet feature and the rest of the counter ratchet surface is occupied by the intermediate section. Also here, the intermediate section may extend from one side of the counter ratchet feature to an opposite side of the counter ratchet feature. The intermediate section may extend all along the circumference of the counter ratchet surface.

The first torque defined by the mutually engaging at least one ratchet feature and the at least one counter ratchet feature may be comparatively large. The at least first torque may be larger than or equal to a maximum torque applicable to at least one of the ratchet member and the counter ratchet member before the ratchet member or counter ratchet member breaks or disintegrates. In other words, the first torque can be as large as a destruction threshold of at least one of the ratchet member and the counter ratchet member. In other words, when the at least one ratchet feature engages with the at least one counter ratchet feature a further rotation of the ratchet feature along the first sense of rotation relative to the counter ratchet feature is effectively blocked or impeded.

The second torque is substantially smaller compared to the first torque. The second torque may be almost zero, namely when the ratchet member is out of engagement from the counter ratchet member and/or when the ratchet member is even out of engagement from an intermediate section of the counter ratchet surface. In some embodiments the second torque may be constant as long as each one of the ratchet features is out of engagement from any of the counter ratchet features. Depending on the mutual mechanical engagement of one of the ratchet features or counter ratchet features with an intermediate section of the other one of the ratchet surface or counter ratchet surface the second torque may be subject to fluctuations or variations as the ratchet member is subject to a rotation relative to the counter ratchet member. The magnitude of the second torque may vary dependent on of the angular position of the ratchet member relative to the counter ratchet member.

In one example the ratchet surface faces towards the counter ratchet surface and the counter ratchet surface faces towards the ratchet surface. Here, the ratchet surface and the counter ratchet surface may face in opposite axial or longitudinal directions. The axial or longitudinal direction may coincide with a center axis of the circular-shaped ratchet member and/or counter ratchet member. The ratchet surface may be provided at an axial or longitudinal end of the ratchet member. The counter ratchet surface may be provided at an axial or longitudinal end of the counter ratchet member.

The ratchet member and the counter ratchet member may be kept in a permanent axial or longitudinal engagement, e.g. by means of a holding force, e.g. provided by a compression spring. In other examples the ratchet member and the counter ratchet member may be of tubular shape and may be arranged axially staggered or interleaved such that a sidewall of one of the ratchet member and counter ratchet member encloses at least a portion of a sidewall of the other one of the ratchet member and the counter ratchet member. Here, the ratchet surface may be provided on an outside facing sidewall portion of the ratchet feature and may be configured to engage with a counter ratchet surface provided on an inside facing portion of a sidewall of the counter ratchet feature.

In an alternative configuration the ratchet surface may be provided on an inside of a sidewall of the tubular-shaped ratchet member and the counter ratchet surface may be provided on an outside of a sidewall of the counter ratchet feature. When the ratchet surface and/or the counter ratchet surface is provided on a radial outside or radial inside surface section of the ratchet member or counter ratchet member, respectively, the ratchet features and counter ratchet features extend radially inwardly and/or radially outwardly.

When the ratchet surface and the counter ratchet surface face in longitudinal direction or axial direction the ratchet features and counter ratchet features extend in longitudinal or axial direction.

According to another example the ratchet member comprises two or more ratchet features that are equidistantly spaced on the ratchet surface. When the ratchet surface comprises an annular shape, e.g. on a flange portion or at a longitudinal end face of the ratchet member the two or more ratchet features may be equiangularly spaced along the circumference of the ratchet surface. In this way, the two or more ratchet features define at least two or more specific angular positions or rotational states of the ratchet member relative to the counter ratchet member from which a dose dispensing may start. The two or more ratchet features of the ratchet member define two or more specific or allowable dose sizes of a dosing mechanism that may be set and subsequently expelled by the injection device.

According to another example the counter ratchet member comprises two or more counter ratchet features that are equidistantly spaced on the counter ratchet surface. When the counter ratchet surface comprises an annular shape, e.g. on a flange portion or on a longitudinal end face of the counter ratchet member the two or more counter ratchet features are equiangularly spaced along the circumference of the counter ratchet surface. In this way and independent of the number of ratchet features of the ratchet member the two or more counter ratchet features define at least two or more specific rotational states or angular positions of the ratchet member relative to the counter ratchet member from which a dose dispensing action may be triggered. The two or more counter ratchet features define two or more specific dose sizes of a dosing mechanism.

In another example the number of ratchet features on the ratchet surface equals a number of counter ratchet features on the counter ratchet surface. When the ratchet features are equidistantly spaced on the ratchet surface and when the counter ratchet features are equidistantly spaced on the counter ratchet surface all ratchet features of the ratchet surface may simultaneously engage with counter ratchet features of the counter ratchet surface. In this way, a torque between the ratchet member and the counter ratchet member can be split, e.g. evenly split, between at least two pairs of ratchet features and counter ratchet features that are in mutual engagement.

The individual mechanical point loads on the individual ratchet features and counter ratchet features can be decreased, thus reducing the risk of mechanical damage of the ratchet features or counter ratchet features. The ratchet mechanism becomes less susceptible to mechanical failure. In addition the ratchet features and counter ratchet features may be dimensioned or configured to withstand a maximum torque that is smaller than the first torque. Since the torque between the ratchet member and the counter ratchet member is always split among at least two pairs of ratchet features and counter ratchet features a maximum torque present at an individual ratchet feature or counter ratchet feature will always be less than the first torque.

According to another example the number of ratchet features on the ratchet surface is larger or smaller than a number of counter ratchet features on the counter ratchet surface. For instance, there may be provided two ratchet features on the ratchet surface and there may be provided only one counter ratchet feature on the counter ratchet surface. In this way two distinct stop positions per revolution of the ratchet feature will be defined, at which one of the ratchet features engages with the counter ratchet feature. In other configurations, there may be provided, e.g. two ratchet features on the ratchet surface and, e.g. three counter ratchet features on the counter ratchet surface. When the ratchet features are equidistantly spaced on the ratchet surface and when the counter ratchet features are equidistantly spaced on the counter ratchet surface there will be provided six discrete stop positions at which one of the ratchet features engages with one of the counter ratchet features.

If the number of ratchet features is non-equal to the number of counter ratchet features the number of ratchet features is not an integer multiple of the number of counter ratchet features and vice versa. Rather, with a non-equal number of ratchet features and counter ratchet features there will be provided a number of discrete stop positions or rotational states of the ratchet member relative to the counter ratchet member that equals to the least common multiple of the number of ratchet features and the number of counter ratchet features. For example, permissible dose sizes and hence corresponding stop configurations of the ratchet member relative to the counter ratchet member could be set to six detent positions, i.e. every 60° with three equispaced ratchet features or counter ratchet features on one of the ratchet member or counter ratchet member and with two counter ratchet features or ratchet features on the other one of the counter ratchet member and the ratchet member.

With another example 15 detent or stop positions, i.e. every 24° could be attained with five equispaced ratchet features or counter ratchet features on the ratchet member or counter ratchet member and three equispaced counter ratchet features or ratchet features on the other one of the counter ratchet member or ratchet member. A non-equal number of equispaced ratchet features and counter ratchet features has the advantage that a modification of only one of the components, ratchet member or counter ratchet member can provide a different type of ratchet mechanism with a different range or size of permissible dose sizes.

For example, the ratchet feature may be implemented as a clutch plate and the counter ratchet member may be implemented as a drive sleeve of an injection device. The non-equal number of ratchet features and counter ratchet features may further have the advantage that the same number of ratchet features and counter ratchet features will be active at each specific detent or stop position to ensure a consistent tactile and audible feedback for the end user of the device.

In another example at least one of the ratchet features and counter ratchet features comprises a tooth protruding from the ratchet surface or counter ratchet surface, respectively. The tooth comprises a first ramped section and a second ramped section opposite to the first ramped section. A ramp angle of the first ramped section differs from a ramp angle of the second ramped section. Typically, each ratchet feature comprises a tooth and each counter ratchet feature comprises a correspondingly shaped tooth. The first ramped section may be steeper than the second ramped section. The first ramped section of the ratchet feature may face along the first sense of rotation and the first ramped section of the counter ratchet feature may face in the opposite direction, hence along the second sense of rotation.

In this way and when reaching a distinct stop position at which the at least one ratchet feature engages with the at least one counter ratchet feature the rather steep first ramped sections of the teeth of the at least one ratchet feature and the at least one counter ratchet feature get in mutual abutment. The ramp angle of the first ramped section is typically larger than 45°. It may be as large as 90° so as to increase the first torque to a mechanical destruction threshold of at least one of the ratchet member or counter ratchet member.

In a further example the second ramped section is less steep than the first ramped section. This allows and supports a rotation of the ratchet feature along the second sense of rotation relative to the counter ratchet feature. At an angular position of the ratchet member relative to the counter ratchet member at which the second ramped sections of the teeth of the ratchet feature and the counter ratchet feature mutually engage a torque required for rotating the ratchet member further along the second sense of rotation is less than the first torque. In this way the ratchet mechanism allows and supports a rotation of the ratchet member relative to the counter ratchet member along the second sense of rotation. As the ratchet tooth of the ratchet feature passes along or slides over a ratchet tooth of the counter ratchet member along the second sense of rotation an audible and/or haptic feedback may be provided thus indicating to the user, that the size of a dose actually set has increased by a predefined step size.

According to another example the circumferential extension of the second ramped section is at least two times or three times larger than a circumferential extension of the first ramped section. For instance, the circumferential extension of the second ramped section is at least four times larger or five times larger than a circumferential extension of the first ramped section. A comparatively large circumferential extension of the second ramped section provides a rather stable and robust tooth of the ratchet feature or counter ratchet feature. This is of particular benefit in situations wherein there is only provided a rather small number of mutually engaged ratchet features and counter ratchet features and when the second torque is comparatively small.

In such configurations the ratchet member may rotate relative to the counter ratchet member at a comparatively large angular velocity and hence with a comparatively large angular momentum. When the at least one ratchet member then mechanically engages with the at least one counter ratchet member a respective angular momentum must be abruptly transferred between the mutually engaging ratchet member and counter ratchet member, in particular between the first ramped sections of the teeth of the mutually engaging ratchet feature and counter ratchet feature. For this and in order to provide increased robustness and stability it is of benefit when the second ramped section comprises a comparatively large circumferential extension, thus providing an increased stability for the respective tooth.

According to another example the intermediate sections of at least one of the ratchet surface and the counter ratchet surface are planar shaped. The intermediate sections may be void of protrusions or recesses. In this way the second torque that is required to rotate the ratchet member relative to the counter ratchet member along the first sense of rotation is comparatively small and remains constant as long as the ratchet features are out of engagement from the counter ratchet features, i.e. when at least one of the ratchet features or counter ratchet features is engaged or is in axial or longitudinal contact with the rather planar shaped intermediate section of the other one of the ratchet feature or counter ratchet feature.

In another example at least one of the ratchet surface and the counter ratchet surface comprises at least one intermediate ratchet feature. The intermediate ratchet feature is provided in or on the intermediate section between the number of ratchet features or between the number of counter ratchet features of the ratchet member or counter ratchet member, respectively. For rotating of the ratchet member relative to the counter ratchet member along the first sense of rotation application of at least a third torque between the ratchet member and the counter ratchet member along the first sense of rotation is required when at least one of the intermediate ratchet features is in engagement with at least one of the ratchet features or counter ratchet features.

Here, the third torque is larger than the second torque and the third torque is smaller than the first torque. In situations at which the ratchet member has been rotated relative to the counter ratchet member along the second sense of rotation to such an extent that the at least one ratchet feature is out of engagement from the at least one counter ratchet feature the ratchet member may be subject to a spring-driven rotation along the first sense of rotation relative to the counter ratchet member. Here, and while being tangentially or circumferentially offset from a counter ratchet feature the ratchet feature may be in mechanical engagement with at least one of the intermediate ratchet features of the intermediate section of the counter ratchet member. Vice versa also a counter ratchet member tangentially or circumferentially offset from a correspondingly shaped ratchet member may be in mechanical engagement with an intermediate ratchet feature or an intermediate section of the ratchet surface.

In this way and as the ratchet member is subject to a rotation along the first sense of rotation, under the action of a depleting torsion spring, the rotational movement of the ratchet member relative to the counter ratchet member is substantially damped or is subject to a braking effect. In this way, the angular momentum or impulse when the at least one ratchet feature engages with the at least one counter ratchet feature can be reduced. Moreover, the angular velocity of the ratchet member rotating relative to the counter ratchet member along the first sense of rotation can be effectively reduced by the at least one intermediate ratchet feature.

Intermediate ratchet features are further benefit to provide an audible and/or haptic feedback to a user and the ratchet member is rotated along the second sense of rotation relative to the counter ratchet member. For instance, the circumferential or tangential distance between adjacently located intermediate ratchet features may correspond to a well-defined step size of a dose of the medicament. For instance, this circumferential or tangential distance may correspond to a standard unit of the medicament.

According to a further example a height of the at least one intermediate ratchet feature is smaller than a height of at least one of the ratchet features and counter ratchet features. Typically, the height, e.g. the longitudinal height or axial protrusion of the ratchet feature substantially equals the respective height or axial or longitudinal dimension of the counter ratchet feature. The intermediate ratchet feature may then comprise a height that is smaller than the height of the ratchet features and the height of the counter ratchet features.

It is generally sufficient when only one of the ratchet surface and the counter ratchet surface comprises at least one or several intermediate ratchet features on the intermediate sections. In other embodiments both of the ratchet surface and the counter ratchet surface comprise intermediate ratchet features of reduced height compared to the height of the ratchet features or counter ratchet features.

The height of intermediate ratchet features of the ratchet member may be equal to the height of intermediate ratchet features of the counter ratchet member. The height of intermediate ratchet features of the ratchet member may also differ from the height of the intermediate ratchet features of the counter ratchet member. In this way, different braking effects could be applied in intermediate angular positions, at which the at least one ratchet feature is out of engagement from the at least one counter ratchet feature.

According to another example the at least one intermediate ratchet feature comprises a tooth protruding from the intermediate section. The tooth comprises a first ramped section and a second ramped section opposite to the first ramped section. A ramp angle of the first ramped section of the at least one intermediate ratchet feature is smaller than a ramp angle of a first ramped section of a tooth of at least one of the ratchet feature or counter ratchet feature. In this configuration the height of the teeth of the intermediate ratchet feature may be equal to or larger than the height of the teeth of the ratchet feature or counter ratchet feature. With a ramp angle of a first ramped section of a tooth of the intermediate ratchet feature smaller than a ramp angle of a first ramped section of a tooth of at least one of the ratchet feature or counter ratchet feature the third torque will be smaller than the first torque.

Insofar there are at least two different ways of how to provide a third torque smaller than the first torque for such angular positions or rotational states of the ratchet member wherein the ratchet features are out of engagement from any of the counter ratchet features. A reduced angular momentum and hence a desired braking effect defining the third torque can be attained by varying at least one of the height or the ramp angle of the teeth of the intermediate ratchet features compared to the ratchet features or counter ratchet features.

According to another example the ratchet member is rotatable along a second sense of rotation against the action of a torsion spring. The torsion spring is configured to apply a driving torque to the ratchet member relative to the counter ratchet member along the first sense of rotation.

The driving torque provided by the torsion spring is smaller than the first torque and the driving torque is larger than the second torque. In this way, and as the ratchet member is rotatable under the action of the depleting torsion spring along the first sense of rotation the ratchet member will be subject to a respective rotation as long as any of the ratchet features is out of engagement from any of the counter ratchet features. As soon as at least one of the ratchet features engages with at least one of the counter ratchet features a rotational movement of the ratchet member relative to the counter ratchet member is stopped.

The number and the arrangement of ratchet features and counter ratchet features on the ratchet surface and counter ratchet surface, respective defines numerous stop positions for the ratchet member relative to the counter ratchet member.

With another example the driving torque provided by the torsion spring is larger than the third torque. In this way the torsion spring is configured to induce a relative rotation of the ratchet member relative to the counter ratchet member as long as any of the ratchet features and any of the counter ratchet features are out of a mutual engagement or as long as any one of the ratchet features is disengaged from any of the counter ratchet features. Since the driving torque inducible by the torsion spring is larger than the third torque the ratchet member may rotate under the action of the spring relative to the counter ratchet member even if at least one of the ratchet features or counter ratchet features is in engagement with at least one of the intermediate ratchet features.

This mutual engagement between the at least one ratchet feature or counter ratchet feature with at least one of the intermediate ratchet features provides a braking effect and thus damps a mechanical shock or angular momentum as the at least one ratchet feature engages with the at least one counter ratchet feature. This may be beneficial for the robustness and durability or endurance of the ratchet mechanism. Mechanical point loads transferred between the ratchet feature and the counter ratchet feature as the ratchet feature and the counter ratchet feature mutually engage under the action of the depleting torsion spring can be thus reduced. A risk of unintentional damage of any of the ratchet member or counter ratchet member can be thus reduced.

According to another aspect the disclosure relates to an injection device for expelling of a number of pre-set or user-selectable doses of a medicament. The injection device comprises an elongated housing extending along a longitudinal axis and configured to accommodate a cartridge. The housing of the injection device may coincide with the housing of the ratchet mechanism. The housing of the ratchet mechanism may form a part or a portion of the housing of the injection device.

The cartridge contains a medicament, typically a liquid medicament and further has a bung sealing a proximal end of the cartridge. Towards the distal end the cartridge has an outlet, e.g. in form of a pierceable septum that can be pierced by a double-tipped piercing assembly configured for releasable assembly to a distal end of the housing of the injection device. The injection device further comprises a piston rod that is configured to urge against the bung along the longitudinal axis in a distal direction relative to the housing. In this way the piston rod is configured to displace the bung relative to the barrel of the cartridge so as to expel a predefined amount of the medicament from the cartridge. The injection device further comprises a dose selector rotatable relative to the housing for setting of a dose.

The injection device further comprises a ratchet mechanism as described above. The ratchet member is rotationally locked to the dose selector at least during setting of the dose and the counter ratchet member is rotationally engageable or is rotationally lockable with at least one of the piston rod and the housing at least for expelling of the dose. The counter ratchet member may be permanently engaged or rotationally locked to the housing. The counter ratchet member may be integrated into the housing and may be unitarily formed with the housing.

In other examples the counter ratchet member is rotationally supported inside the housing. In such examples the counter ratchet member may be engaged with the piston rod for transferring a driving torque to the piston rod and for urging the piston rod in distal direction.

Typically, the injection device is switchable between a dose setting mode and a dose dispensing mode. For this, the injection device may comprise a trigger or a dose button. Upon depressing of the trigger or dose button, e.g. in distal direction, a dose previously set by the dose selector can be dispensed or expelled. During a dose dispensing action the counter ratchet member may be rotationally locked to the piston rod so as to induce a torque onto the piston rod. The piston rod may be further in threaded engagement with the housing so that a rotation of the piston rod induced by the counter ratchet member leads to a distally advancing motion of the piston rod relative to the housing and hence relative to the barrel of the cartridge.

During dose setting the counter ratchet member may be steadfastly connected to the housing. It may be at least temporally lockable to the housing. During dose dispensing this connection may be released so that the counter ratchet member is enabled to rotate during dose dispensing and for transferring a driving torque or a driving force to the piston rod.

During dose dispensing the ratchet mechanism may be locked. The ratchet member and the counter ratchet member may be rotationally locked, e.g. through the mutual engagement of the ratchet member and the counter ratchet member, e.g. via mutually corresponding ratchet features and counter ratchet features. During dose expelling at least one of the ratchet member and the counter ratchet member is subject to a rotation relative to the housing along the first sense of rotation. In particular, the counter ratchet member is rotatable relative to the housing at least during expelling of the dose and for urging the piston rod against the bung During dose dispensing at least the ratchet member is subject to a rotation along the second sense of rotation. The second sense of rotation may be a rotation in a clockwise direction as seen from a proximal end of the device. For setting of a dose and for increasing of a dose the dose selector may be rotatable along the second sense of rotation, hence in clockwise direction to set a dose of predefined size.

Typically, at least one of the dose selector and the ratchet member is connected with one end of a torsion spring. An opposite end of the torsion spring may be connected to the housing. Rotating of at least one of the dose selector and the ratchet member along the second sense of rotation occurs against the action of the torsion spring. During dose dispensing the torsion spring may store energy. When released or as long as none of the ratchet features is in engagement with any one of the counter ratchet features the torsion spring is configured to rotate the counter ratchet feature along the first sense of rotation until at least one of the ratchet features engages with at least one of the counter ratchet features.

The mutual engagement and hence the geometric design of the mutually engaging ratchet surface and counter ratchet surface define at least one or numerous angular positions of the ratchet feature from which a dispensing action may start. In all other angular positions of the ratchet member that are selectable by rotating of the dose selector the ratchet mechanism is in an unstable state, in which the ratchet member is driven by the torsion spring along the first sense of rotation until at least one of the ratchet features engages with at least one of the counter ratchet features.

The injection device may be implemented as a disposable injection device intended to be discarded in its entirety after the content of the cartridge has been used up. With a disposable injection device the cartridge filled with the medicament is pre-assembled inside the housing of the injection device. With disposable injection devices the housing or components thereof are non-detachable and non-openable.

With other examples the injection device is configured as a reusable injection device. Here, the cartridge can be replaced after use. For this, the housing of the injection device typically comprises a proximally located body to accommodate the dose setting mechanism and a drive mechanism of the injection device and further comprises a distally located cartridge holder that is configured to accommodate the cartridge. The cartridge holder and the body of the housing can be detachably connected, e.g. by a snap-fit connection or by a screw connection.

In some examples at least one of the ratchet feature and the counter ratchet feature is fixed in longitudinal direction relative to the housing. At least one of the ratchet feature and the counter ratchet feature may be urged or may be spring supported by a clutch spring in longitudinal direction so as to keep the ratchet surface in permanent engagement or permanent abutment with the counter ratchet surface. Specifically for rotating at least one of the ratchet member and the counter ratchet member along the second sense of rotation, e.g. during setting of a dose at least a small but distinct longitudinal sliding displacement of at least one of the ratchet member and the counter ratchet member may be supported by the clutch spring.

Moreover, it is conceivable, that the torsion spring exhibits a varying driving torque depending on the degree of rotation of the ratchet member relative to the counter ratchet member or relative to the housing of an injection device. For instance and for a rotation of the ratchet member by a rather small angle of rotation the driving torque provided by the torsion spring may be smaller than the third torque. In this way and when releasing the ratchet member the ratchet mechanism will remain in a stable state from which a dispensing action may start. As the torsion spring is rotated further along the second sense of rotation and as the torsion spring is biased further the driving torque may increase and may become larger than the third torque. In such an angular range a stable state of the ratchet mechanism can be only obtained when at least one of the ratchet features engages with at least one of the counter ratchet features. If a dose above a predefined minimum dose is set by a user only a reduced number of specific or predefined dose sizes can be set and dispensed. If a dose below the minimum threshold is dialled every generally available dose size can be set and dispensed by the injection device.

In the present context a distal end or distal direction refers to that end section of the injection device from which the liquid medicament is expelled. The proximal end or proximal direction refers to that end section of the injection device which is furthest away from biological tissue of a patient to be treated with the medicament. The injection device is typically configured for administration of a liquid medicament, such as insulin or heparin. The injection device is typically configured for self-medication. It is configured for operation by only one hand of a user. The trigger typically provided at the proximal end of the injection device is configured to be depressed by a thumb of a user while residual fingers of the same hand may grip the housing of the injection device.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl- ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2, des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4 (1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4 (1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4 (1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(02)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(02) 25, Asp28] Exendin-4(1-39)-NH2,
des Pro36, Pro37, Pro38 [Met(O)14, Trp(02)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(02) 25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the art that various modifications and variations can be made to the present disclosure without departing from the scope of the present disclosure as it is defined by the claims. Further, it is to be noted, that any reference numerals used in the appended claims are not to be construed as limiting the scope of the disclosure.

BRIEF DESCRIPTION OF THE FIGURES

In the following various embodiments of a data collection device in connection with an injection device are described by making reference to the drawings, in which:

FIG. 21 shows the torsion spring of the device of FIG. 1; and

FIGS. 22a-c show different embodiments of the threads between the piston rod and the housing of the device of FIG. 1.

DETAILED DESCRIPTION

Figure 1:
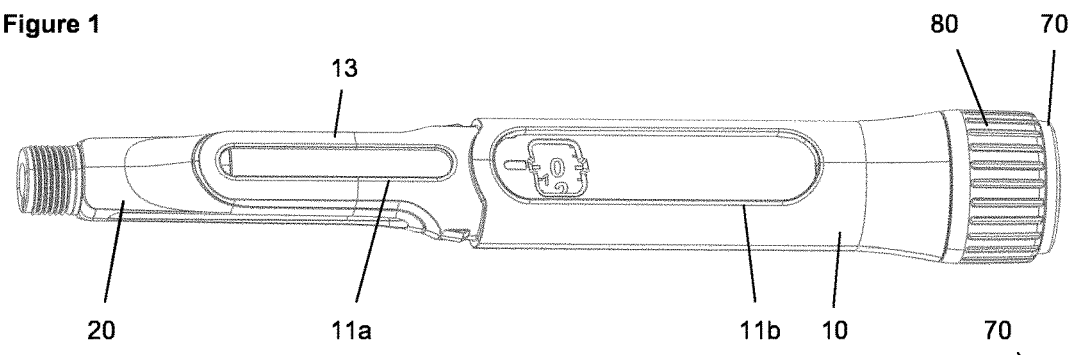
FIG. 1 shows a top view of the drug delivery device of the present disclosure in the minimum dose position.
Figure 2:
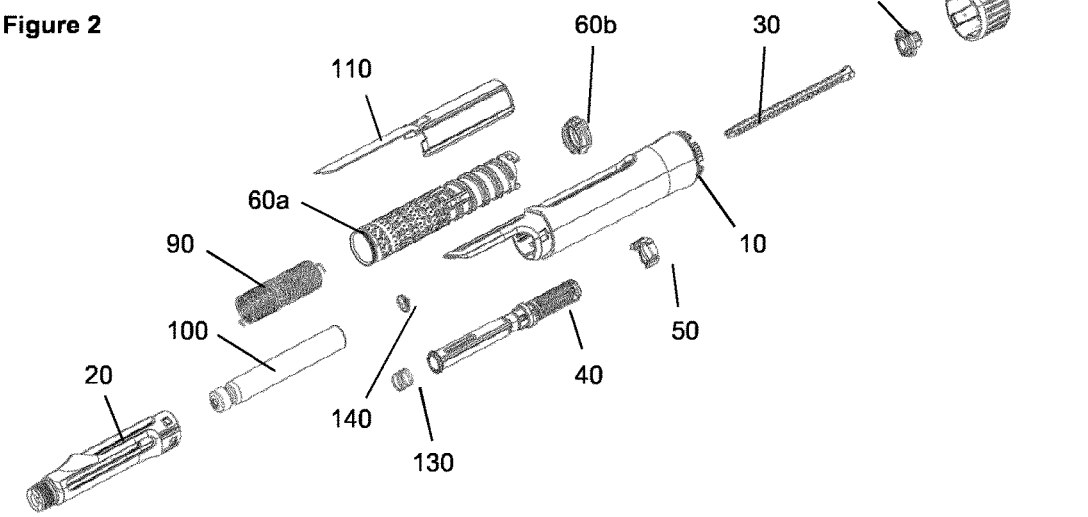
FIG. 2 shows an exploded view of the components of the device of FIG. 1.
Figure 3:
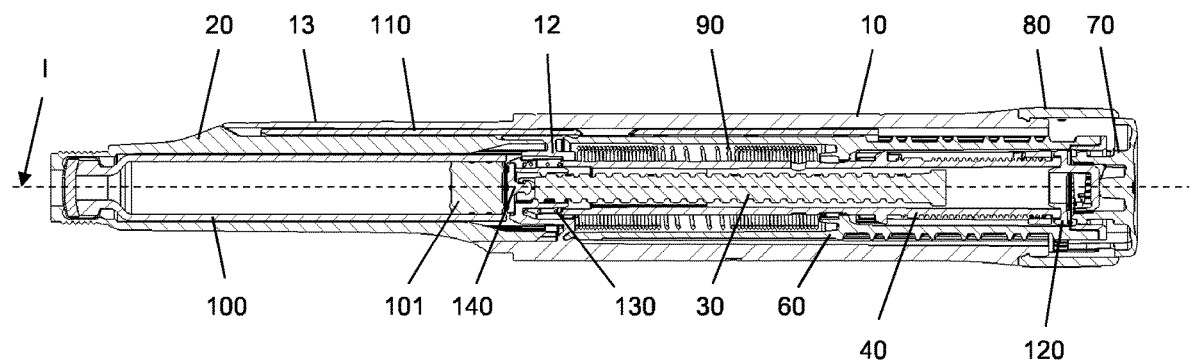
FIG. 3 shows a sectional view of the device of FIG. 1.

FIG. 1 shows a drug delivery device in the form of an injection pen. The device has a distal end (left end in FIG. 1) and a proximal end (right end in FIG. 1). The component parts of the drug delivery device are shown in FIG. 2. The drug delivery device comprises a body or housing 10, a cartridge holder 20, a lead screw (piston rod) 30, a drive sleeve 40, a nut 50, a dose indicator (number sleeve) 60, a button 70, a dial grip or dose selector 80, a torsion spring 90, a cartridge 100, a gauge element 110, a clutch plate 120, a clutch spring 130 and a bearing 140. A needle arrangement (not shown) with a needle hub and a needle cover may be provided as additional components, which can be exchanged as explained above. All components are located concentrically about a common principal axis I of the mechanism which is shown in FIG. 3.

The housing 10 or body is a generally tubular element having a proximal end with an enlarged diameter. The housing 10 provides location for the liquid medication cartridge 100 and cartridge holder 20, windows 11a, 11b for viewing the dose number on the number sleeve 60 and the gauge element 110, and a feature on its external surface, e.g. a circumferential groove, to axially retain the dose selector

80. A flange-like or cylindrical inner wall 12 comprises an inner thread engaging the piston rod 30. The housing 10 further has at least one internal, axially orientated slot or the like for axially guiding the gauge element 110. In the embodiment shown in the Figures, the distal end is provided with an axially extending strip 13 partly overlapping cartridge holder 20. The Figures depict the housing 10 as a single housing component. However, the housing 10 could comprise two or more housing components which may be permanently attached to each other during assembly of the device.

The cartridge holder 20 is located at the distal side of housing 10 and permanently attached thereto. The cartridge holder may be a transparent or translucent component which is tubular to receive cartridge 100. The distal end of cartridge holder 20 may be provided with means for attaching a needle arrangement. A removable cap (not shown) may be provided to fit over the cartridge holder 20 and may be retained via clip features on the housing 10.

Figure 8:
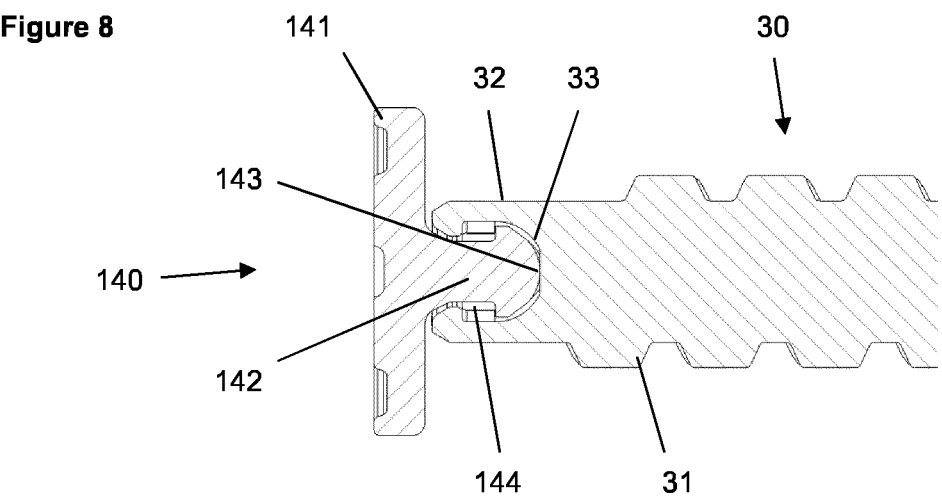
FIG. 8 shows an interface between the piston rod and a bearing of the device of FIG. 1.

The piston rod 30 is rotationally constrained to the drive sleeve 40 via a splined interface. When rotated, the piston rod 30 is forced to move axially relative to the drive sleeve 40, through its threaded interface with the inner wall 12 of housing 10. The lead screw 30 is an elongate member with an outer thread 31 (FIG. 3) engaging the corresponding thread of the inner wall 12 of housing 10. The thread 31 may have a large lead-in, for example a wedge shape form, at its distal end to engage a corresponding housing thread form on the first rotation. The interface comprises at least one longitudinal groove or track and a corresponding protrusion or spline 45 of the driver 40. At its distal end, the lead screw 30 is provided with an interface for clip attachment of the bearing 140. In the present embodiment, this interface comprises two clip arms 32 extending in the distal direction defining an insertion space between them for insertion of a bearing 140 interface. As an alternative, the interface may comprise only one single clip arm extending more than 180° about the longitudinal axis, or may comprise one or several clip arms 32. The clip arm(s) 32 may have a bent form with a recessed clip portion as shown in FIG. 8. Preferably, the clip arm(s) form a cylindrical outer face having a diameter equal to or smaller than the outer diameter of the lead screw 30 at the base of the groove (flute base) of the outer thread 31. A concave contact surface 33 is provided between the clip arms 32 for abutment of a corresponding portion of bearing 140.

The drive sleeve 40 is a hollow member surrounding the lead screw 30 and arranged within number sleeve 60. It extends from an interface with the clutch plate 120 to the contact with the clutch spring 130. The drive sleeve 40 is axially movable relative to the housing 10, the piston rod 30 and the number sleeve 60 in the distal direction against the bias of clutch spring 130 and in the opposite proximal direction under the bias of clutch spring 130.

Figure 18:
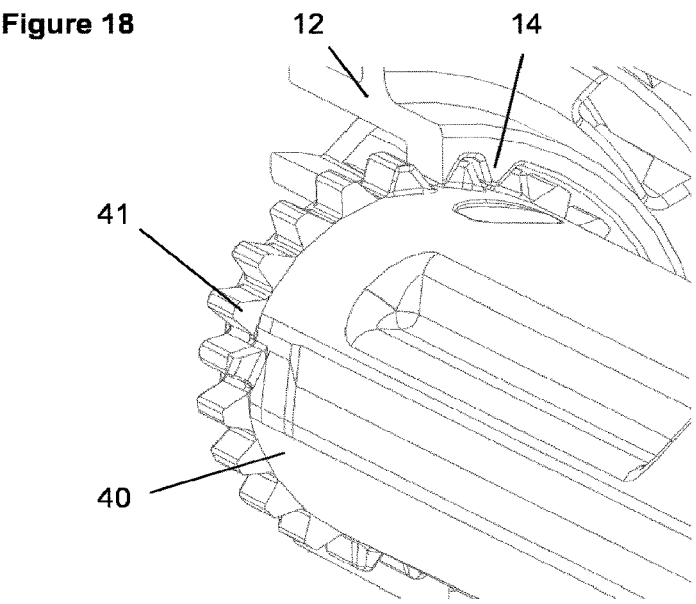
FIG. 18 shows an interface between the housing and the drive sleeve of the device of FIG. 1.

A splined tooth interface with the housing 10 prevents rotation of the drive sleeve 40 during dose setting. This interface which is shown in FIG. 18 in detail comprises a ring of radially extending outer teeth 41 at the distal end of drive sleeve 40 and corresponding radially extending inner teeth 14 of the housing component 10. When the button 70 is pressed, these drive sleeve 40 to housing 10 spline teeth 14, 41 are disengaged allowing the drive sleeve 40 to rotate relative to housing 10.

A further splined tooth interface with the number sleeve 60 is not engaged during dialling, but engages when the button 70 is pressed, preventing relative rotation between the drive sleeve 40 and number sleeve 60 during dispense.

Figure 7A:
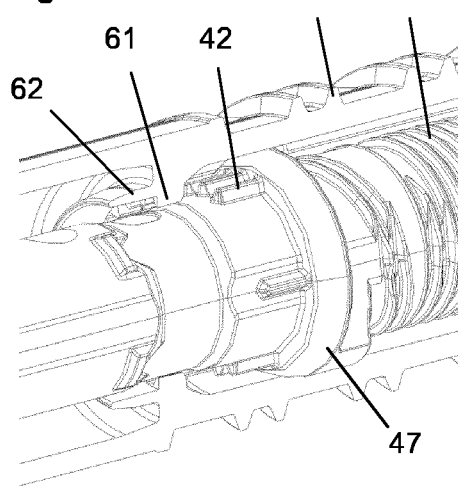
FIGS. 7a, b show an interface between the number sleeve and the drive sleeve of the device of FIG. 1 in the dose setting mode and in the dose dispensing mode.
Figure 7B:
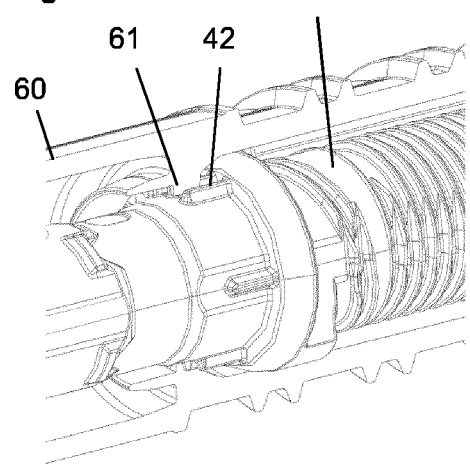

In the preferred embodiment shown in FIGS. 7a and 7b this interface comprises inwardly directed splines 61 on a flange 62 on the inner surface of the number sleeve 60 and a ring of radially extending outer splines 42 of drive sleeve 40. The corresponding splines 61, 42 are located on the number sleeve 60 and the drive sleeve 40, respectively, such that axial movement of the drive sleeve 40 relative to the (axially fixed) number sleeve 60 engages or disengages the splines to rotationally couple or decouple the drive sleeve 40 and the number sleeve 60.

Preferably, the splines 61, 42 are arranged such that they are decoupled when teeth 41 of drive sleeve 40 and inner teeth 14 of housing component 10 mesh and engage when teeth 41 and inner teeth 14 disengage. In a preferred embodiment the splines 61, 42 are longer in the axial direction compared with teeth 41, 14. This allows engagement of the splines 61, 42 shortly before disengagement of teeth 41, 14. In other words, the splines 61, 42 and the teeth 41, 14 are designed and arranged such that actuation of the button 70 rotationally constrains the drive sleeve 40 to the number sleeve 60 before the drive sleeve 40 is allowed to rotate relative to housing 10. Similarly, as the button 70 is released after dose dispensing axial movement of the drive sleeve 40 first rotationally constrains the drive sleeve 40 to the housing and thereafter decouples splines 61, 42. As an alternative to the corresponding splines 61, 42 teeth may be provided. As a further alternative or in addition to splines 61, 42, drive sleeve 40 and number sleeve 60 may be rotationally coupled to each other during dose dispensing via clutch plate 120.

Figure 19:
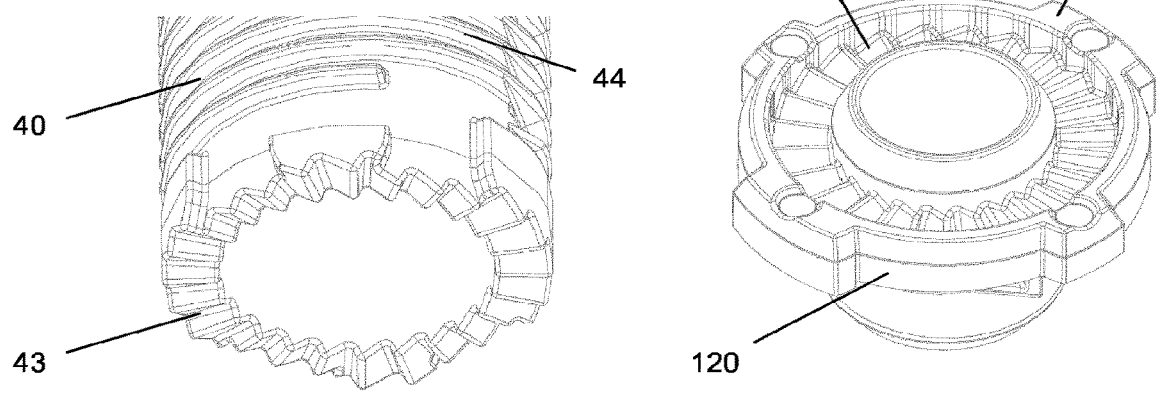
FIG. 19 shows an interface between the clutch plate and the drive sleeve of the device of FIG. 1.

An interface of the drive sleeve 40 which is shown in FIG. 19 comprises a ring of ratchet teeth 43 located at the proximal end face of drive sleeve 40 and a ring of corresponding ratchet teeth 121 of clutch plate 120.

Figure 20:
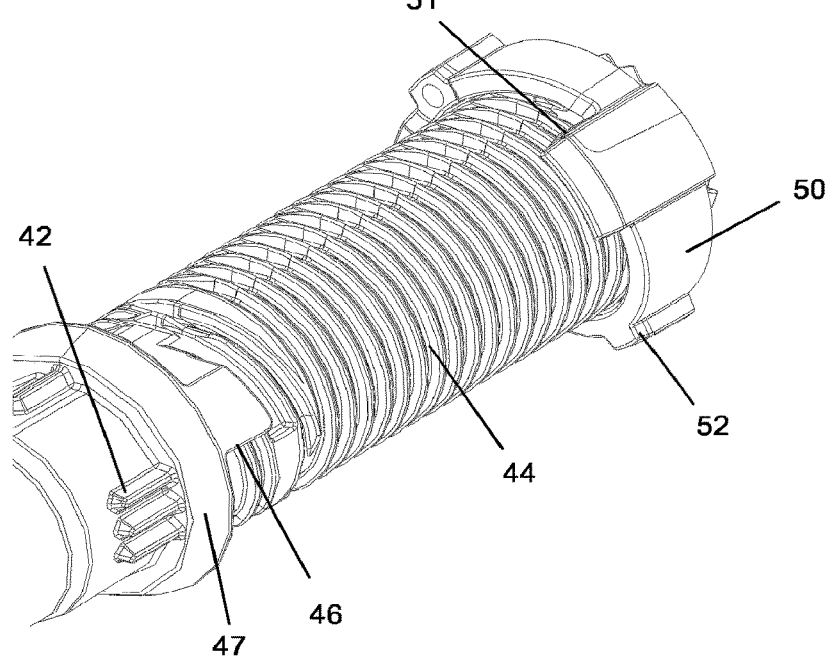
FIG. 20 shows a last dose mechanism of the device of FIG. 1.

The driver 40 has a threaded section 44 providing a helical track for the nut 50 (FIG. 20). In addition, a last dose abutment or stop 46 is provided which may be the end of the thread 44 track or preferably a rotational hard stop for interaction with a corresponding last dose stop 51 of nut 50, thus limiting movement of the nut 50 on the thread 44. At least one longitudinal spline 45 engages a corresponding track of the lead screw 30. Further, the drive sleeve is provided with a ramp 47 interacting with a clicker arm 67 when the drive sleeve 40 is in its distal position during dose dispensing, i.e. when button 70 is depressed.

The last dose nut 50 is located between the number sleeve 60 and the drive sleeve 40. It is rotationally constrained to the number sleeve 60, via a splined interface (splines 52 on nut 50). It moves along a helical path relative to the drive sleeve 40, via a threaded interface (thread 44), when relative rotation occurs between the number sleeve 60 and drive sleeve 40 which is during dialling only. This is shown in FIG. 20. As an alternative, the nut 50 may be splined to the driver 40 and threaded to the number sleeve 60. In the embodiment shown in the Figures, the nut 50 is a full nut, but in alternative embodiments it may be a half nut, i.e. a component extending approximately 180° around the center axis of the device. A last dose stop 51 is provided engaging stop 46 of drive sleeve 40 when a dose is set corresponding to the remaining dispensable amount of medicament in the cartridge 100.

The dose indicator or number sleeve 60 is a tubular element as shown in FIGS. 2 and 3. The number sleeve 60 is rotated during dose setting (via dose selector 80) and dose correction and during dose dispensing by torsion spring 90. Together with gauge element 110 the number sleeve 60 defines a zero position ('at rest') and a maximum dose position. Thus, the number sleeve 60 may be seen as a dose setting member.

For manufacturing reasons the number sleeve 60 of the embodiment shown in the Figures comprises a number sleeve lower 60*a* which is rigidly fixed to a number sleeve upper 60*b* during assembly to form the number sleeve 60. Number sleeve lower 60*a* and number sleeve upper 60*b* are separate components only to simplify number sleeve 60 mould tooling and assembly. As an alternative, the number sleeve 60 may be a unitary component. The number sleeve 60 is constrained to the housing 10 by features towards the distal end to allow rotation but not translation. The number sleeve lower 60*a* is marked with a sequence of numbers, which are visible through the gauge element 110 and the openings 11*a*, 11*b* in the housing 10, to denote the dialled dose of medicament.

Further, the number sleeve lower 60*a* has a portion with an outer thread 63 engaging the gauge element 110. End stops 64, 65 are provided at the opposite ends of thread 63 to limit relative movement with respect to the gauge element 110.

Figure 5:
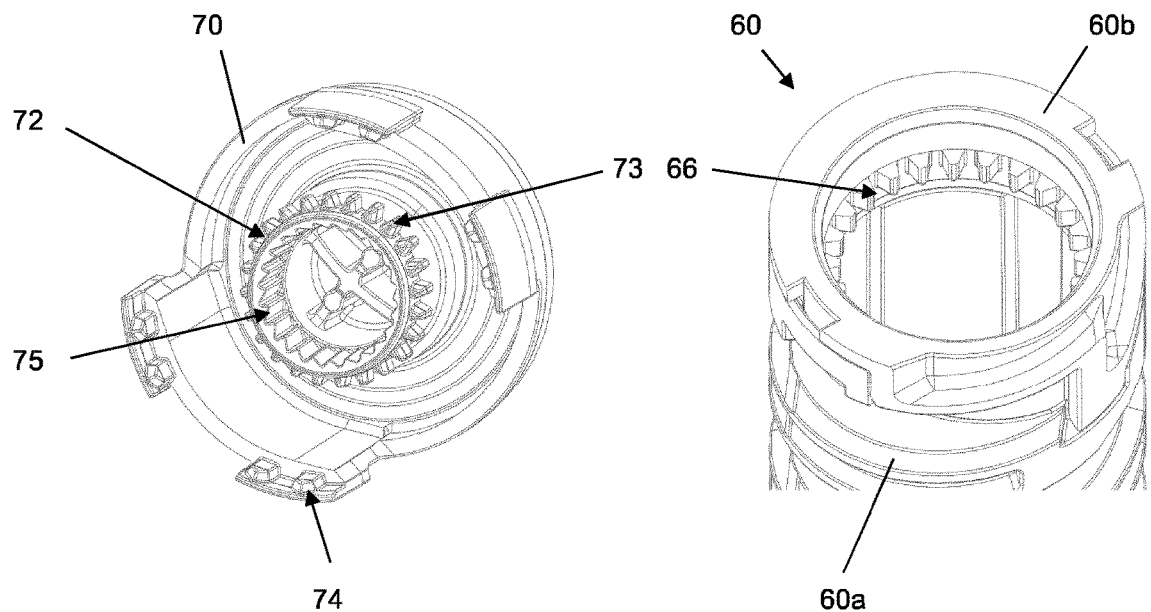
FIG. 5 shows an interface between the number sleeve and the button of the device of FIG. 1.

Clutch features which have the form of a ring of splines 66 in the embodiment of FIG. 5 are provided inwardly directed on number sleeve upper 60*b* for engagement with splines 73 of the button 70 during dose setting and dose correction. A clicker arm 67 is provided on the outer surface of number sleeve 60 which interacts with the drive sleeve 40 and the gauge member 110 for generating a feedback signal. In addition, the number sleeve lower 60*a* is rotationally constrained to the nut 50 and to the clutch plate 120 via a splined interface comprising at least one longitudinal spline.

An interface for attachment of the torsion spring 90 to the number sleeve lower 60*a* comprises large lead-ins and a groove feature 68 with a pocket 69 or anchor point for receiving a first coil or hook portion of the spring. The groove 68 has an end feature in the form of a ramp that is in interference with the hook portion 91 of the spring. The design of the groove 68 is such that the spring 90 may be received within the pocket 69 without interfering with the gauge element 110.

Figure 6:
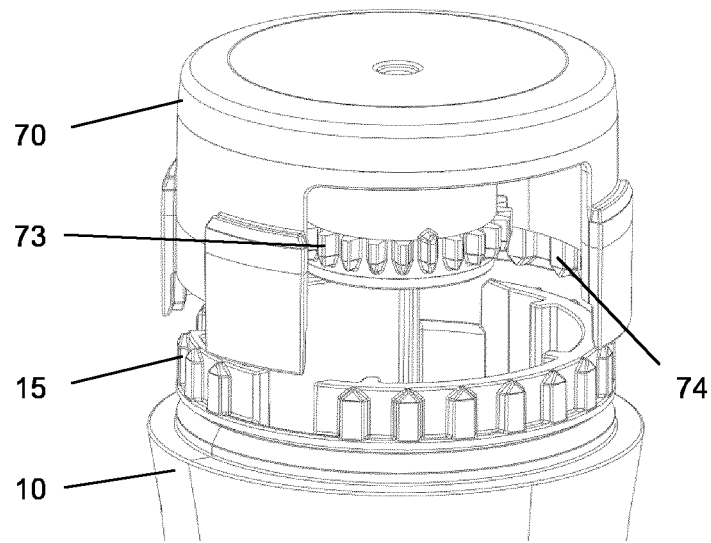
FIG. 6 shows an interface between the housing and the button of the device of FIG. 1.

The button 70 which forms the proximal end of the device is permanently splined to the dose selector 80. A central stem 71 extends distally from the proximal actuation face of the button 70. The stem 71 is provided with a flange 72 carrying the splines 73 for engagement with splines 66 of the number sleeve upper 60*b* (FIG. 5). Thus, it is also splined via splines 66, 73 (FIG. 5) to the number sleeve upper 60*b* when the button 70 is not pressed, but this spline interface is disconnected when the button 70 is pressed. The button 70 has a discontinuous annular skirt with splines 74. When the button 70 is pressed, splines 74 on the button 70 engage with splines on the housing 10 (FIG. 6), preventing rotation of the button 70 (and hence the dose selector 80) during dispense. These splines 74, 15 disengage when the button 70 is released, allowing a dose to be dialled. Further, a ring of ratchet teeth 75 is provided on the inner side of flange 72 (FIG. 9) for interaction with clutch plate 120.

The dose selector 80 is axially constrained to the housing 10. It is rotationally constrained, via the splined interface, to the button 70. This splined interface which includes grooves interacting with spline features formed by the annular skirt of button 70 remains engaged irrespective of the dose button 70 axial positions. The dose selector 80 or dose dial grip is a sleeve-like component with a serrated outer skirt.

Figure 16:
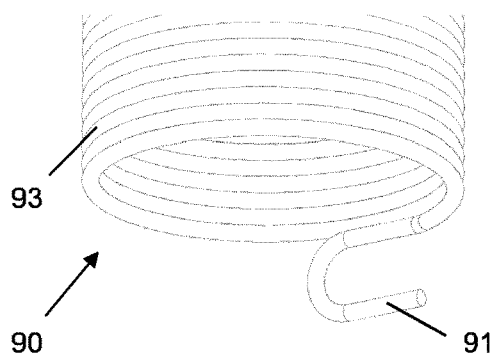
FIG. 16 shows a portion of the drive spring of the device of FIG. 1.

The torsion spring 90 is attached at its distal end to the housing 10 and at the other end to the number sleeve 60. The torsion spring 90 is located inside the number sleeve 60 and surrounds a distal portion of the drive sleeve 40. As shown in FIG. 16, the spring has a hook 91 at one end for attachment on the number sleeve 60. A similar hook end 92 is provided at the opposite end for attachment on the housing 10. The torsion spring 90 is pre-wound upon assembly, such that it applies a torque to the number sleeve 60 when the mechanism is at zero units dialled. The action of rotating the dose selector 80, to set a dose, rotates the number sleeve 60 relative to the housing 10, and charges the torsion spring 90 further.

The torsion spring 90 is formed from a helical wire with at least two different pitches. In FIG. 21, both ends are formed from 'closed' coils 93, i.e. the pitch equals the wire diameter and each coil contacts the adjacent coil. The central portion has 'open' coils 94, i.e. the coils do not contact each other.

The cartridge 100 is received in cartridge holder 20 (FIG. 3). The cartridge 100 may be a glass ampoule having a moveable rubber bung 101 at its proximal end. The distal end of cartridge 100 is provided with a pierceable rubber seal which is held in place by a crimped annular metal band. In the embodiment depicted in the Figures, the cartridge 100 is a standard 1.5 ml cartridge. The device is designed to be disposable in that the cartridge 100 cannot be replaced by the user or health care professional. However, a reusable variant of the device could be provided by making the cartridge holder 20 removable and allowing backwinding of the lead screw 30 and the resetting of nut 50.

The gauge element 110 is constrained to prevent rotation but allow translation relative to the housing 10 via a splined interface. The gauge element 110 has a helical feature 111 on its inner surface which engages with the helical thread cut in the number sleeve 60 such that rotation of the number sleeve 60 causes axial translation of the gauge element 110. This helical feature on the gauge element 110 also creates stop abutments 112, 113 against the end of the helical cut in the number sleeve 60 to limit the minimum and maximum dose that can be set.

The gauge element 110 has a generally plate or band like component having a central aperture 114 or window and two flanges 115, 116 extending on either side of the aperture. The flanges 115, 116 are preferably not transparent and thus shield or cover the number sleeve 60, whereas the aperture 114 or window allows viewing a portion of the number sleeve lower 60*a*. Further, gauge element 110 has a cam 117 and a recess 118 (FIGS. 11*a*-12*c*) interacting with the clicker arm 67 of the number sleeve 60 at the end of dose dispensing.

Figure 9:
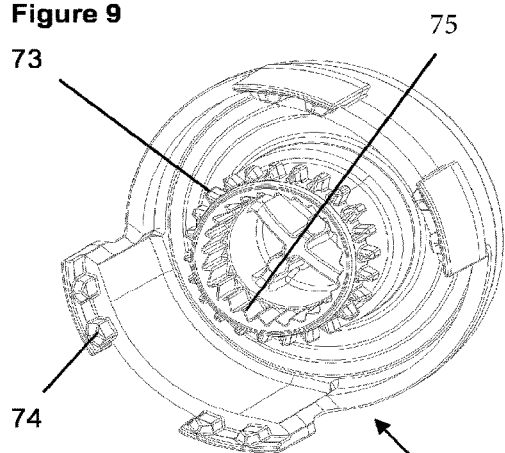
FIG. 9 shows an interface between the clutch plate and the button of the device of FIG. 1.
Figure 9:
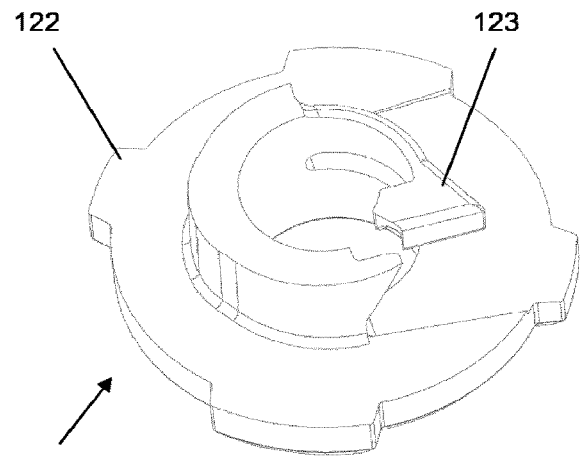
Figure 10:
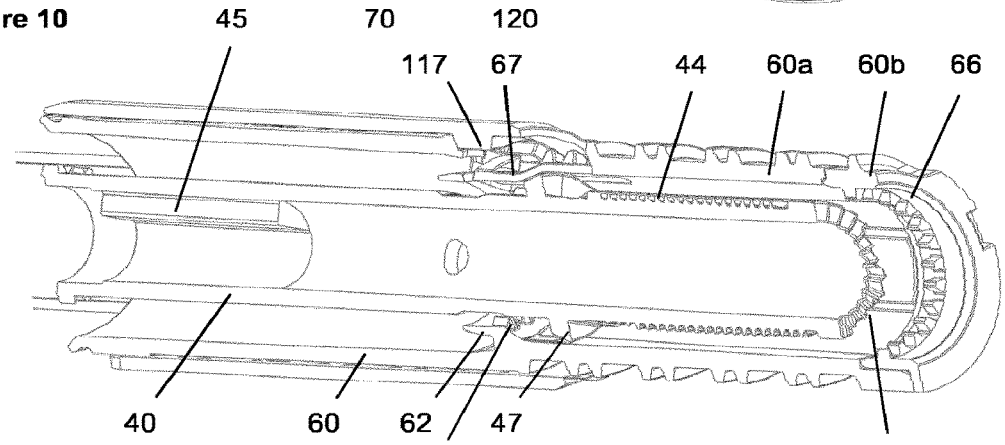
FIG. 10 shows in a sectional view the components of an end of dose clicker of the device of FIG. 1.

As can be seen in FIGS. 9 and 19, the clutch plate 120 is a ring-like component. The clutch plate 120 is splined to the number sleeve 60 via splines 122. It is also coupled to the drive sleeve 40 via a ratchet interface (ratchet teeth 43, 121). The ratchet provides a detented position between the number sleeve 60 and drive sleeve 40 corresponding to each dose unit, and engages different ramped tooth angles during clockwise and anti-clockwise relative rotation. A clicker arm 123 is provided on the clutch plate 120 for interaction with ratchet features 75 of the button.

The clutch spring 130 is a compression spring. The axial position of the drive sleeve 40, clutch plate 120 and button 70 is defined by the action of the clutch spring 130, which applies a force on the drive sleeve 40 in the proximal direction. This spring force is reacted via the drive sleeve 40, clutch plate 120, and button 70, and when 'at rest' it is further reacted through the dose selector 80 to the housing 10. The spring force ensures that the ratchet interface (ratchet teeth 43, 121) is always engaged. In the 'at rest' position, it also ensures that the button splines 73 are engaged with the number sleeve splines 66, and the drive sleeve teeth 41 are engaged with teeth 14 of the housing 10.

The bearing 140 is axially constrained to the piston rod 30 and acts on the bung 101 within the liquid medicament cartridge. It is axially clipped to the lead screw 30, but free to rotate. The bearing 140 comprises a disc 141 having a stem 142 extending in the proximal direction. The stem 142 has at its proximal end a convex contact surface 143. In addition, a recessed portion 144 is provided on the stem 142. The curvature of the convex contact surface 143 and the concave contact surface 33 is chosen such that the contact diameter between the bearing 140 and lead screw 30 is small to minimize the frictional losses at this interface. The design of the clip interface between bearing 140 and lead screw 30 permits the lead screw 30 to be assembled axially, from the proximal end and through the thread engagement to the housing 10, which simplifies assembly. In addition, this design allows a simple "open and shut" mould tooling for both components.

Figure 4A:
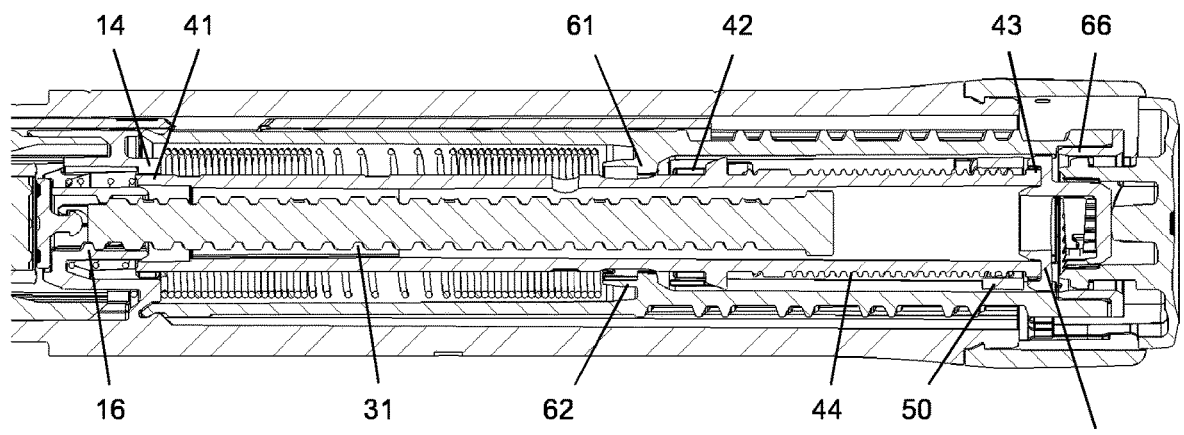
FIG. 4a shows an enlarged sectional view of a detail of the device of FIG. 1 in the dose setting mode.
Figure 4B:
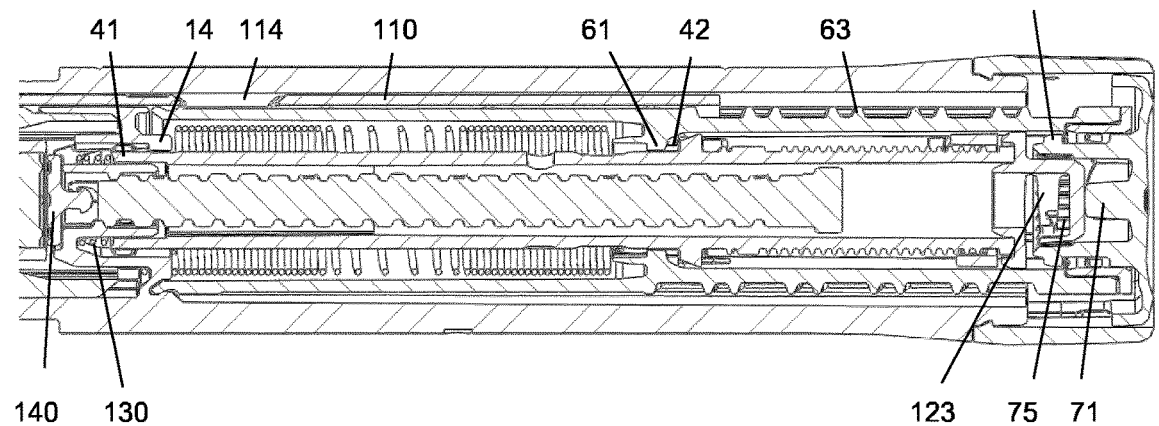
FIG. 4b shows an enlarged sectional view of a detail of the device of FIG. 1 in the dose dispensing mode.
Figure 17A:
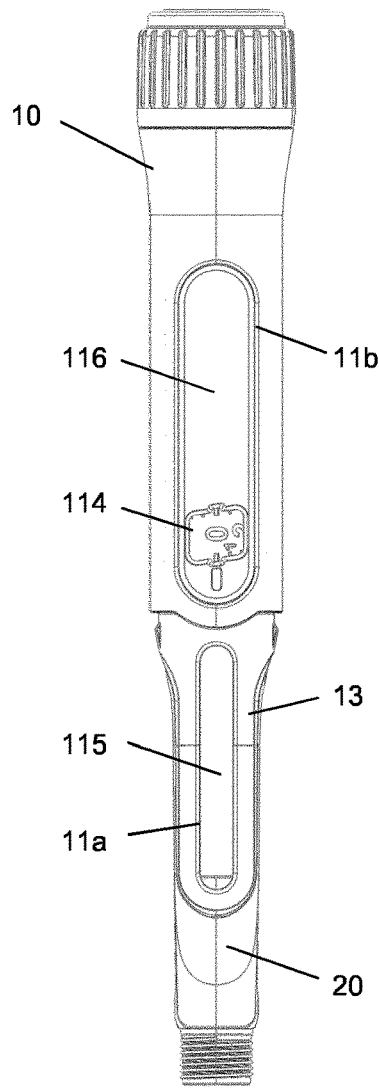
FIGS. 17a, b show top views of the device of FIG. 1 with 0 units dialled and with 96 units dialled.

With the device in the 'at rest' condition as shown in FIGS. 4a and 17a, the number sleeve 60 is positioned against its zero dose abutment 64, 113 with the gauge element 110 and the button 70 is not depressed. Dose marking '0' on the number sleeve 60 is visible through the windows 11b and 114 of the housing 10 and gauge element 110, respectively.

The torsion spring 90, which has a number of pre-wound turns applied to it during assembly of the device, applies a torque to the number sleeve 60 and is prevented from rotating by the zero dose abutment 64, 113. It is also possible to 'back-wind' the mechanism slightly due to an offset between the zero dose stop 64, 113 and the angular offset of the drive sleeve 40 spline teeth. This has the effect of preventing possible weepage when a dose is dialled and the zero dose abutment is disengaged.

The automated assembly of the torsion spring 90 into the number sleeve 60 can be achieved by incorporating large lead-ins and a groove feature to the number sleeve 60. As the torsion spring 90 is rotated during assembly, the hook end form 91 locates in the groove feature before engaging the anchor point in the number sleeve 60. To help to prevent the torsion spring 90 disengaging the anchor point 69 during subsequent assembly steps it is possible to create an interference between the torsion spring 90 and the number sleeve 60, or a one-way clip feature.

The user selects a variable dose of liquid medicament by rotating the dose selector 80 clockwise, which generates an identical rotation in the number sleeve 60. Rotation of the number sleeve 60 causes charging of the torsion spring 90, increasing the energy stored within it. As the number sleeve 60 rotates, the gauge element 110 translates axially due to its threaded engagement thereby showing the value of the dialled dose. The gauge element 110 has flanges 115, 116 either side of the window area 114 which cover the numbers printed on the number sleeve 60 adjacent to the dialled dose to ensure only the set dose number is made visible to the user.

A specific feature of this disclosure is the inclusion of a visual feedback feature in addition to the discrete dose number display typical on devices of this type. The distal end (flange 115) of the gauge element 110 creates a sliding scale through a small window 11a in the housing 10. As an alternative, the sliding scale could be formed using a separate component engaged with the number sleeve 60 on a different helical track.

As a dose is set by the user, the gauge element 110 translates axially, the distance moved proportional to the magnitude of the dose set. This feature gives clear feedback to the user regarding the approximate size of the dose set. The dispense speed of an auto-injector mechanism may be higher than for a manual injector device, so it may not be possible to read the numerical dose display during dispense. The gauge feature provides feedback to the user during dispense regarding dispense progress without the need to read the dose number itself. For example, the gauge display may be formed by an opaque element on the gauge element 110 revealing a contrasting coloured component underneath. Alternatively, the revealable element may be printed with coarse dose numbers or other indices to provide more precise resolution. In addition, the gauge display simulates a syringe action during dose set and dispense.

Figure 17B:
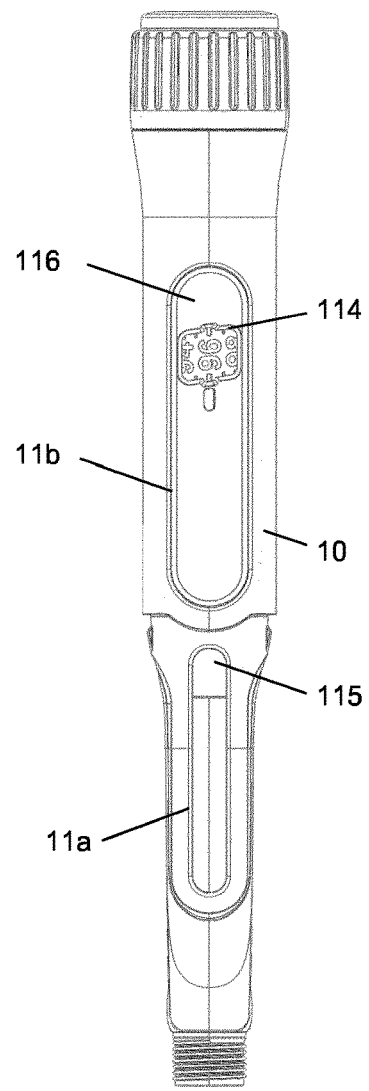

The openings 11a, 11b in the housing 10 allow the user to view the gauge feature and number display as shown in FIGS. 17a and 17b. To reduce dust ingress and prevent the user from touching moving parts, these openings 11a, 11b are covered by translucent windows. These windows may be separate components, but in this embodiment they are incorporated into the housing 10 using 'twin-shot' moulding technology. A first shot of translucent material forms the internal features and the windows 11a, 11b, and then a 'second shot' of opaque material forms the outer cover of the housing 10.

The mechanism utilises a dose selector 80 with an increased diameter relative to the housing 10 which aids dialling although this is not a requirement of the mechanism. This feature is particularly useful (but not essential) for an auto-injector mechanism where a power supply is charged during dose setting and the torque required to turn the dose selector 80 may be higher than for a non-auto injector device.

The drive sleeve 40 is prevented from rotating as the dose is set and the number sleeve 60 rotated, due to the engagement of its splined teeth 41 with teeth 14 of the housing 10. Relative rotation must therefore occur between the clutch plate 120 and drive sleeve 40 via the ratchet interface 43, 121.

The user torque required to rotate the dose selector 80 is a sum of the torque required to wind up the torsion spring 90, and the torque required to overhaul the ratchet interface 43, 121. The clutch spring 130 is designed to provide an axial force to the ratchet interface 43, 121 and to bias the clutch plate 120 onto the drive sleeve 40. This axial load acts to maintain the ratchet teeth engagement of the clutch plate 120 and drive sleeve 40. The torque required to overhaul the ratchet teeth 43, 121 in the dose set direction is a function of the axial load applied by the clutch spring 130, the clockwise ramp angle of the ratchet teeth 43, 121, the friction coefficient between the mating surfaces and the mean radius of the ratchet interface 43, 121.

As the user rotates the dose selector 80 sufficiently to increment the mechanism by one increment, the number sleeve 60 rotates relative to the drive sleeve 40 by one ratchet tooth. At this point the ratchet teeth 43, 121 re-engage into the next detented position. An audible click is generated by the ratchet re-engagement, and tactile feedback is given by the change in torque input required.

Relative rotation of the number sleeve 60 and the drive sleeve 40 is allowed as splines 42, 61 are disengaged during dose setting. This relative rotation also causes the last dose nut 50 to travel along its threaded path, towards its last dose abutment on the drive sleeve 40.

With no user torque applied to the dose selector 80, the number sleeve 60 is now prevented from rotating back under the torque applied by the torsion spring 90, solely by the ratchet interface 43, 121 between the clutch plate 120 and the drive sleeve 40. The torque necessary to overhaul the ratchet in the anti-clockwise direction is a function of the axial load applied by the clutch spring 130, the anti-clockwise ramp angle of the ratchet, the friction coefficient between the mating surfaces and the mean radius of the ratchet features. The torque necessary to overhaul the ratchet must be greater than the torque applied to the number sleeve 60 (and hence clutch plate 120) by the torsion spring 90. The ratchet ramp angle is therefore increased in the anti-clockwise direction to ensure this is the case whilst ensuring the dial-up torque is as low as possible.

The user may now choose to increase the selected dose by continuing to rotate the dose selector 80 in the clockwise direction. The process of overhauling the ratchet interface 43, 121 between the number sleeve 60 and drive sleeve 40 is repeated for each dose increment. Additional energy is stored within the torsion spring 90 for each dose increment and audible and tactile feedback is provided for each increment dialled by the re-engagement of the ratchet teeth. The torque required to rotate the dose selector 80 increases as the torque required to wind up the torsion spring 90 increases. The torque required to overhaul the ratchet in the anti-clockwise direction must therefore be greater than the torque applied to the number sleeve 60 by the torsion spring 90 when the maximum dose has been reached.

If the user continues to increase the selected dose until the maximum dose limit is reached, the number sleeve 60 engages with its maximum dose abutment 65 on the maximum dose abutment 112 of gauge element 110. This prevents further rotation of the number sleeve 60, clutch plate 120 and dose selector 80.

Depending on how many increments have already been delivered by the mechanism, during selection of a dose, the last dose nut 50 may contact its last dose abutment 51 with stop face 46 of the drive sleeve 40. The abutment prevents further relative rotation between the number sleeve 60 and the drive sleeve 40, and therefore limits the dose that can be selected. The position of the last dose nut 50 is determined by the total number of relative rotations between the number sleeve 60 and drive sleeve 40, which have occurred each time the user sets a dose.

With the mechanism in a state in which a dose has been selected, the user is able to deselect any number of increments from this dose. Deselecting a dose is achieved by the user rotating the dose selector 80 anti-clockwise. The torque applied to the dose selector 80 by the user is sufficient, when combined with the torque applied by the torsion spring 90, to overhaul the ratchet interface 43, 121 between the clutch plate 120 and drive sleeve 40 in the anti-clockwise direction. When the ratchet is overhauled, anti-clockwise rotation occurs in the number sleeve 60 (via the clutch plate 120), which returns the number sleeve 60 towards the zero dose position, and unwinds the torsion spring 90. The relative rotation between the number sleeve 60 and drive sleeve 40 causes the last dose nut 50 to return along its helical path, away from the last dose abutment.

With the mechanism in a state in which a dose has been selected, the user is able to activate the mechanism to commence delivery of a dose. Delivery of a dose is initiated by the user depressing the button 70 axially in the distal direction.

When the button 70 is depressed, splines between the button 70 and number sleeve 60 are disengaged, rotationally disconnecting the button 70 and dose selector 80 from the delivery mechanism, i.e. from number sleeve 60, gauge element 110 and torsion spring 90. Splines 74 on the button 70 engage with splines 15 on the housing 10, preventing rotation of the button 70 (and hence the dose selector 80) during dispense. As the button 70 is stationary during dispense, it can be used in the dispense clicker mechanism as shown in FIG. 9. A stop feature in the housing 10 limits axial travel of the button 70 and reacts any axial abuse loads applied by the user, reducing the risk of damaging internal components.

The clutch plate 120 and drive sleeve 40 travel axially with the button 70. This engages the splined tooth interface 42, 61 between the drive sleeve 40 and number sleeve 60 as shown in FIGS. 7a (splines 42, 61 disengaged) and 7b (splines 42, 61 engaged), preventing relative rotation between the drive sleeve 40 and number sleeve 60 during dispense. The splined tooth interface 41, 14 between the drive sleeve 40 and the housing 10 disengages, so the drive sleeve 40 can now rotate and is driven by the torsion spring 90 via the number sleeve 60, and clutch plate 120.

Rotation of the drive sleeve 40 causes the piston rod 30 to rotate due to their splined engagement, and the piston rod 30 then advances due to its threaded engagement to the housing 10. The number sleeve 60 rotation also causes the gauge element 110 to traverse axially back to its zero position whereby the zero dose abutment 64, 113 stops the mechanism.

The bearing 140 is axially clipped to the piston rod 30, but free to rotate. Since the bearing 140 is in direct contact with the bung 101, it does not rotate as the piston rod 30 rotates and advances during dose dispense. As described above, the contact diameter between the bearing 140 and piston rod 30 is small to minimise the frictional losses at this interface. The design of the piston rod 30 and bearing 140 eliminates delicate clip features or large contact diameters present on previous concepts. This embodiment also allows the piston rod 30 to be assembled axially, from the proximal end and through the thread engagement to the housing 10, which simplifies assembly.

Tactile feedback during dose dispense is provided via the compliant cantilever clicker arm 123 integrated into the clutch plate 120. This arm 123 interfaces radially with ratchet features 75 on the inner surface of the button 70, whereby the ratchet tooth spacing corresponds to the number sleeve 60 rotation required for a single increment dispense. During dispense, as the number sleeve 60 rotates and the button 70 is rotationally coupled to the housing 10, the ratchet features 75 engage with the clicker arm 123 to produce an audible click with each dose increment delivered.

Delivery of a dose continues via the mechanical interactions described above while the user continues to depress the button 70. If the user releases the button 70, the clutch spring 130 returns the drive sleeve 40 to its 'at rest' position (together with the clutch plate 120 and button 70), engaging the splines 14, 41 between the drive sleeve 40 and housing 10, preventing further rotation and stopping dose delivery.

During delivery of a dose, the drive sleeve 40 and number sleeve 60 rotate together, so that no relative motion in the last dose nut 50 occurs. The last dose nut 50 therefore travels axially relative to the drive sleeve 40 during dialling only.

Once the delivery of a dose is stopped, by the number sleeve 60 returning to the zero dose abutment, the user may release the button 70, which will re-engage the spline teeth 14, 41 between the drive sleeve 40 and housing 10. The mechanism is now returned to the 'at rest' condition.

It is possible to angle the spline teeth 14, 41 on either the drive sleeve 40 or housing 10 so that when the button 70 is released the re-engagement of the spline teeth 14, 41 fractionally 'backwinds' the drive sleeve 40 thereby removing the engagement of the number sleeve 60 to the zero dose stop abutment on the gauge element 110. This compensates for the effect of clearances in the mechanism (for example due to tolerances) which could otherwise lead to slight advancement of the piston rod 30 and medicament dispense when the device is dialled for the subsequent dose due to the number sleeve 60 zero dose stop not restraining the mechanism and instead the restraint returning to the splines between the drive sleeve 40 and housing 10.

At the end of dose dispensing, additional audible feedback is provided in the form of a 'click', distinct from the 'clicks' provided during dispense, to inform the user that the device has returned to its zero position via the interaction of the clicker arm 67 on the number sleeve 60 with the ramp 47 on the drive sleeve 40 and the cam 117 and the recess 118 on the gauge element 110. This embodiment allows feedback to only be created at the end of dose delivery and not created if the device is dialled back to, or away from, the zero position.

Figure 11A:
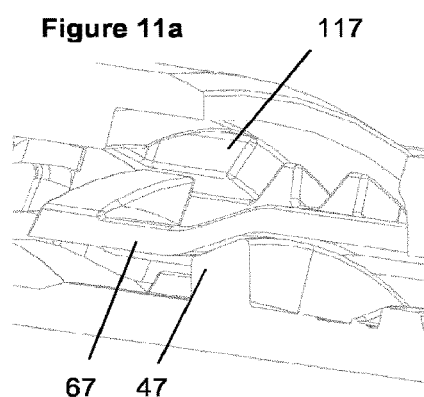
FIGS. 11a-c show in enlarged views the sequence of generating a click at the end of dose dispensing of the device of FIG. 1.

FIG. 11*a* shows the position of the click features when the device is in the 'at rest' condition, with zero units dialled and the button 70 not depressed. It can be seen that the cam feature 117 on the gauge element 110 does not contact the clicker arm 67 on the number sleeve 60 when the button 70 is in the 'at rest' condition, so during storage or dialling the clicker arm 67 is not deflected.

During dialling, the gauge element 110 translates in the proximal direction, so the cam 117 is no longer aligned axially with the clicker arm 67. At the start of dose delivery when the drive sleeve 40 translates in the distal direction, the ramp 47 on the drive sleeve 40 pushes the clicker arm 67 radially outwards. During dose delivery, the gauge element 110 translates back in the distal direction, and towards the end of dose delivery, the clicker arm 67 contacts the cam 117 on the gauge element 110. For small doses, the cam 117 and clicker arm 67 will be in contact at the start of the dose. FIGS. 11*b* to 12*c* show the component interactions. After dose delivery, the button 70 is released and the end of dose mechanism returns to its 'at rest' position.

Figure 11B:
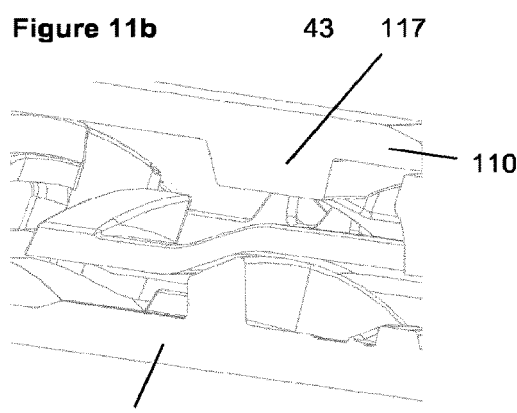
Figure 11C:
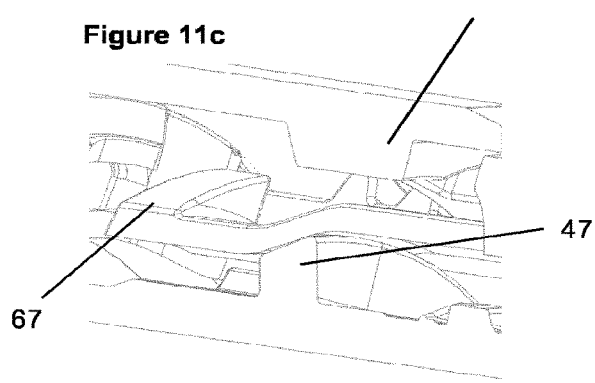

In FIG. 11*b* a dose is dialled and approximately one full dial turn is applied to number sleeve 60. Gauge element 110 is axially translated away from zero unit position, so that cam 117 is no longer aligned axially with clicker arm 67. FIG. 11*c* shows the start of dispensing, when button 70 is depressed to initiate dose dispense and which causes the drive sleeve 40 to translate axially. Ramp 47 on the drive sleeve 40 pushes clicker arm 67 radially out and into radial alignment with cam 117 on the gauge element 110.

Figure 12A:
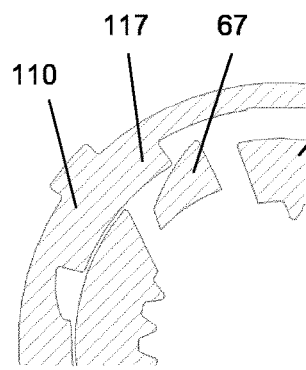
FIGS. 12a-c show in enlarged sectional views the sequence of generating a click at the end of dose dispensing of the device of FIG. 1.
Figure 12B:
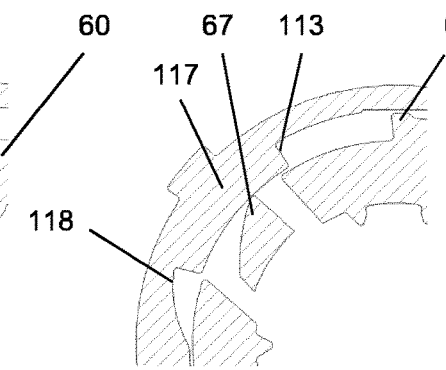
Figure 12C:
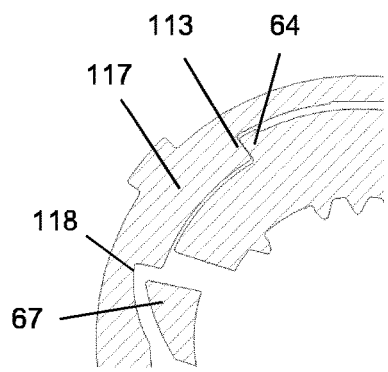
Figure 13:
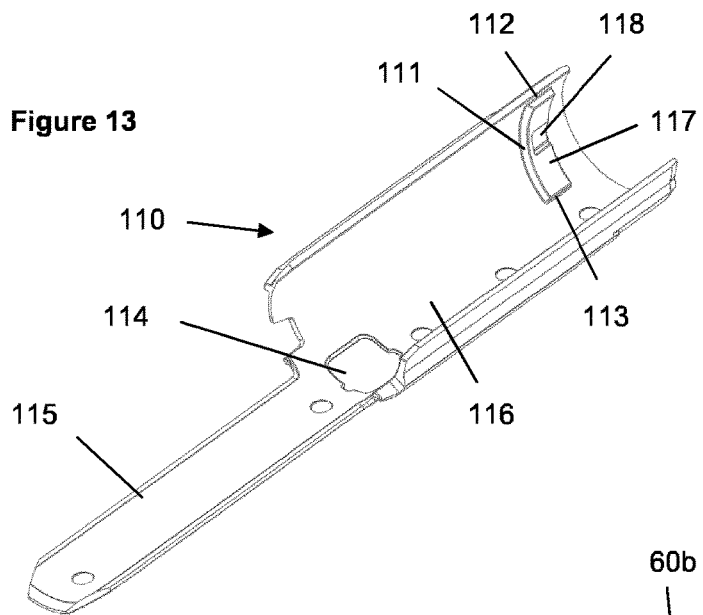
FIG. 13 shows the gauge element of the device of FIG. 1.
Figure 14:
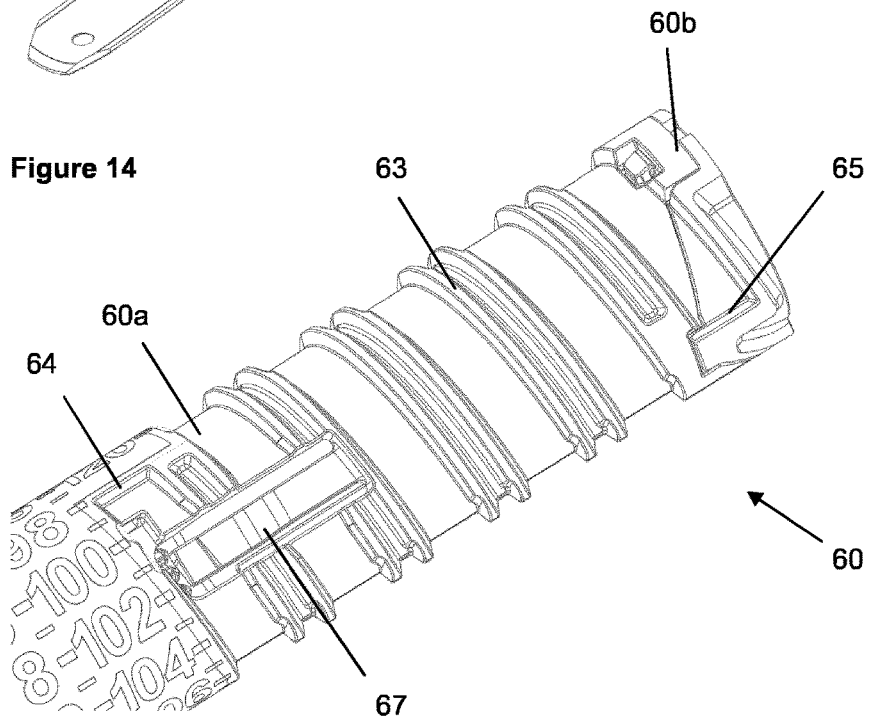
FIG. 14 shows a portion of the number sleeve of the device of FIG. 1.
Figure 15:
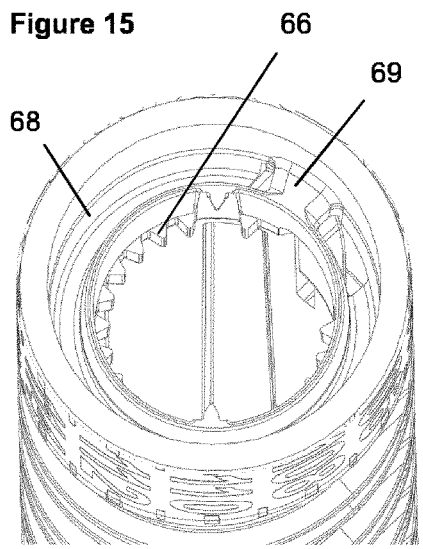
FIG. 15 shows a further portion of the number sleeve of the device of FIG. 1.

FIG. 12*a* shows the mechanism at the end of dose dispensing with approximately 4 units remaining. The gauge element 110 returns axially towards its zero unit position, so that cam 117 aligns axially with clicker arm 67. Rotation of number sleeve 60 causes clicker arm 67 to contact cam 117 such that clicker arm 67 is pushed radially inwards. With approximately 2 units remaining the number sleeve 60 rotates further and clicker arm 67 follows the profile of cam 117 (FIG. 12*b*). This radial deflection 'charges' clicker arm 67 storing elastic energy. In FIG. 12*c* dispensing is completed as the number sleeve 60 reaches its zero unit rotational position. The clicker arm 67 drops off the sharp edge of cam 117 into recess 118. Elastic energy is released causing clicker arm 67 to spring radially outwards to contact cam 117 and create a distinct 'click'.

In the principal embodiment of this disclosure, the lead screw 30 advances by a fixed displacement for each revolution of the drive sleeve 40. In other embodiments, the rate of displacement may vary. For example, the lead screw 30 may advance a large displacement per revolution to dispense a first amount of medicament from the cartridge 100 and then a smaller displacement per revolution to dispense the rest of the cartridge 100. This is advantageous, as it can compensate for the fact that the first dose dispensed from the cartridge 100 often has a lower volume than other doses, for a given displacement of the mechanism.

FIG. 22 shows three embodiments with the threads 16 of the housing 10 and the threads 31 of the lead screw 30 projected around the circumference. Arrow R indicates the direction of revolution of the lead screw 30 with respect to housing 10 for all three views.

View (a) shows the principal embodiment, where the pitch is equal on the housing 10 and lead screw 30, so the lead screw 30 advances a fixed amount for every revolution of the drive sleeve 40. In view (b), the first turn of thread 31 on the lead screw 30 has a large pitch, and the other turns have a small pitch. During the first revolution, the lead screw 30 displacement depends on the large pitch of the first turn of thread 31 on the lead screw 30, so it displaces a large amount per revolution. For subsequent revolutions the lead screw 30 displacement depends on the smaller pitch of the lead screw thread 31, so it displaces a smaller amount. In view (c), the housing 10 thread 16 has a larger pitch than the lead screw 30. During the first revolution, the lead screw 30 displacement depends on the pitch of the housing thread 16, so it displaces a large amount per revolution. For subsequent revolutions the lead screw 30 displacement depends on the pitch of the lead screw thread 31, so it displaces a smaller amount.

In one embodiment, the drug delivery device comprises a dose setting mechanism for setting a minimum dose size. Such a dose setting mechanism should ensure that the user cannot dispense less medicament than required.

As already described above, the drug delivery device comprises a number sleeve 60 which rotates in one direction, which is the dose setting direction, during dose setting. The number sleeve 60 rotates in the reverse direction during dispensing or correction of the set dose. The gauge element 110 engages the thread 63 on the number sleeve 60, resulting in an axial movement in the dose setting direction during setting and in the reverse direction during dispensing or correction.

One example of a ratchet mechanism 200 is illustrated in FIGS. 23-27. The ratchet mechanism 200 comprises a circular-shaped ratchet member 220 and a circular-shaped counter ratchet member 240. The ratchet member comprises a sleeve-like shape and the counter ratchet member also comprises a tubular or sleeve-like shape. The ratchet member 220 comprises a ratchet surface 221 provided with a number of ratchet features 222, 224 and with a number of intermediate sections 223, 225 located between the ratchet features 222, 224. The ratchet features 222, 224 are identically shaped. They may also be of different shape. Each one of the ratchet features 222, 224 comprises a ratchet tooth 226. As it is apparent from the side view of FIG. 27 the ratchet tooth 226 comprises a non-symmetric shape along a circumferential direction. The ratchet tooth 226 comprises a first ramped section 226*a* and a second ramped section 226*b*. The first ramped section 226*a* is rather steep and the second ramped section 226*b* is comparatively shallow. The ramp angle of the first ramped section 226*a* is larger than the ramp angle of the second ramped section 226*b*.

Figure 25:
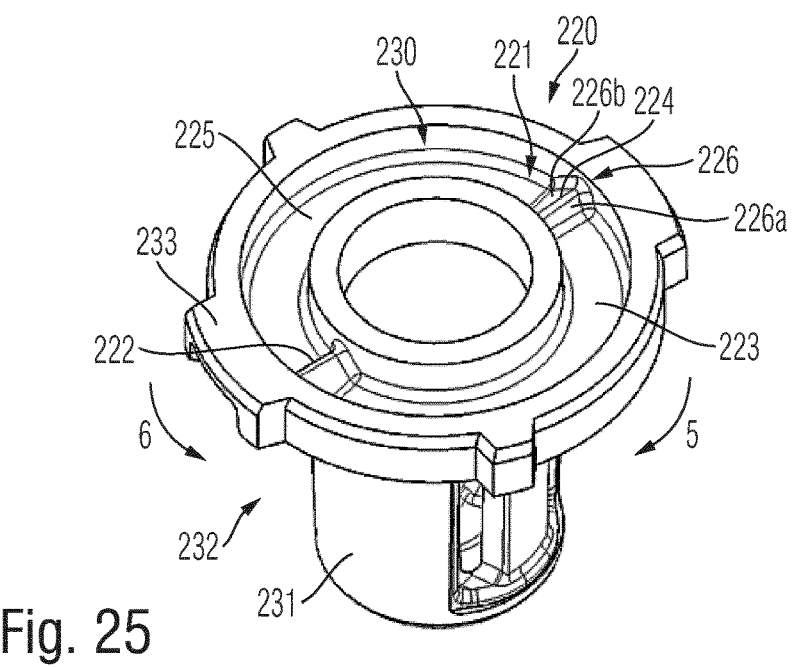
FIG. 25 is a perspective view of the ratchet member.

As indicated in FIG. 25 the ratchet surface 221 is of annular shape. It may be located on the bottom of an annular groove 230 at a longitudinal end face of the ratchet member 220. The ratchet member 220 comprises a tubular-shaped stem section 231 and a circular-shaped flange section 232 located at a longitudinal end of the stem section 231. The radial extension of the flange section 232, hence the diameter of the flange section 232 is larger than the radial extent or the diameter of the stem section 231. There are provided protrusions 233 protruding radially outwardly from the flange section 232. These protrusions are configured to form a splined interface with the number sleeve 60 of the injection device as described above in connection with FIGS. 1-22.

In one example the ratchet member 220 replaces the clutch plate 120 of the injection device as described in connection with FIGS. 1-22. Insofar, any features, benefits and mechanical interactions as described above in connection with the clutch plate 120 equally apply to the ratchet member 220, 320 as described below in connection with the FIGS. 26-30.

The counter ratchet member 240, 340 as described below and as shown in the FIGS. 23-30 is equivalent to the driver 40 as described above in connection with the FIGS. 1-22. The driver 40 is effectively replaced by the counter ratchet member 240, 340. Any features, benefits and mechanical interaction as described above in connection with the driver 40 equally apply to the counter ratchet member 240, 340.

Figure 23:
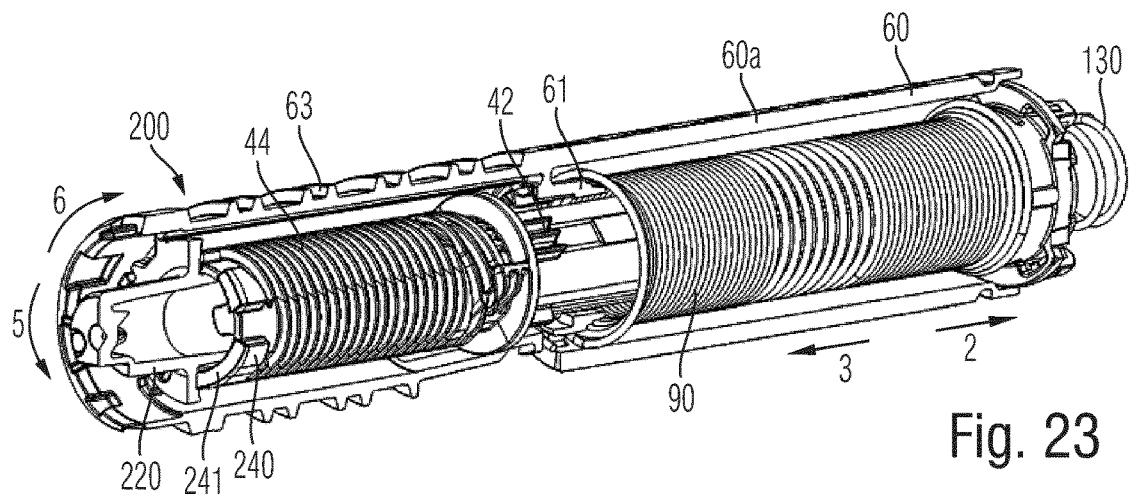
FIG. 23 shows a schematic perspective illustration of one example of the ratchet mechanism of the injection device.
Figure 24:
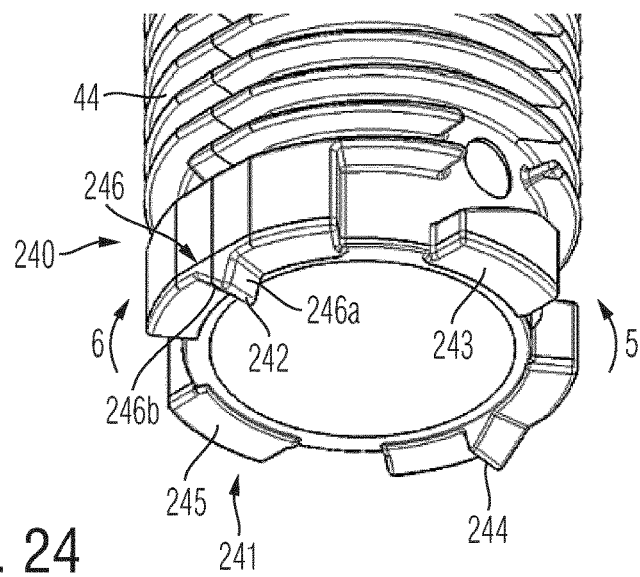
FIG. 24 is a perspective view of the counter ratchet member.

As it is apparent from a comparison of FIGS. 23-25 the ratchet surface 221 forms a distal end face of the ratchet member 220.

The counter ratchet member 240 also comprises a counter ratchet surface 241 facing towards the ratchet surface 221. The ratchet surface 221 and the counter ratchet surface 241 are and remain in axial abutment through the action of the clutch spring 130. The counter ratchet surface 241 faces in proximal direction 3. The ratchet surface 221 faces in distal direction 2.

Figure 27:
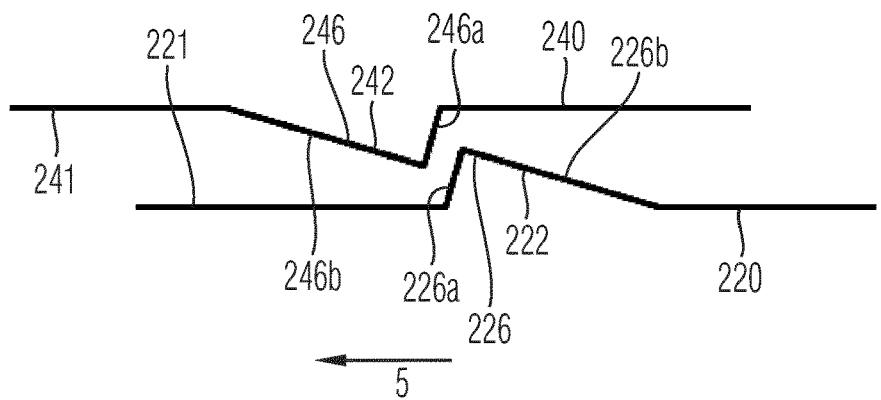

As indicated in FIG. 24 the counter ratchet surface 241 is provided with a number of counter ratchet features 242, 244. Each one of the counter ratchet features 242, 244 comprises a counter ratchet tooth 246. As illustrated in FIG. 27 each one of the counter ratchet teeth 246 comprises a first ramped section 246a and a second ramped section 246b. Also here, the first ramped section 246a is steeper than the second ramped section 246b.

During setting of a dose, e.g. by rotating the dose selector 80 the ratchet member 220 is subject to a rotation along a second sense of rotation 6 relative to the housing 10 and/or relative to the counter ratchet member 240, e.g. in clockwise direction so as to increase the size of a dose to be set and to be expelled by the injection device 1. Rotation of the dose selector 80 along the second sense of rotation 6 leads to a respective rotation of the ratchet member 220 along the second sense of rotation 6 and hence to a respective rotation of the dose indicator 60 along the second sense of rotation 6. The torsion spring 90 operably engaged with the dose indicator 60 is biased further and tends to rotate the dose indicator 60 along the opposite sense of rotation, hence along the first sense of rotation 5.

The ratchet mechanism 200 formed by the mutual engagement of the ratchet surface 221 and the counter ratchet surface 241 provides a kind of a slip clutch that only engages at a few distinct angular or rotational states of the ratchet member 220 relative to the counter ratchet member 240. These distinct rotational states of the ratchet member are defined by the geometry and the position of the ratchet features 222, 224 and the correspondingly shaped counter ratchet features 242, 244.

As indicated in FIGS. 24 and 25 there are provided only two ratchet features 222, 224 on the ratchet surface 221 and there are provided only two correspondingly shaped counter ratchet features 242, 244 on the counter ratchet surface 241. The ratchet features 222, 224 and the counter ratchet features 242, 244 are configured to engage with their first ramped sections 226a, 246a as the ratchet member 220 is rotated along the first sense of rotation 5 relative to the counter ratchet member, hence as the ratchet member 220 is rotated under the action of the depleting torsion spring 90.

In a configuration as indicated in FIG. 27, in which at least one of the ratchet features 222, 224 engages with at least one of the counter ratchet features 242, 244 a further rotation of the ratchet member 220 relative to the counter ratchet member 240 along the first sense of rotation 5 is only possible if a torque above at least a first torque M1 is applied to the ratchet member 220 relative to the counter ratchet member 240. The ramp angle of the first ramped sections 226a, 246a may be as large as 90° with regard to the plane of the ratchet surface 221 or counter ratchet surface 241. In this case, the first torque M1 will be larger than or equal to a mechanical destruction level of at least one of the ratchet member 220 and the counter ratchet member 240.

The mutual engagement of the at least one ratchet feature 222, 224 of the ratchet member 220 with at least one counter ratchet features 242, 244 of the counter ratchet member 240 will define a stop position for the rotation of the ratchet member 220 under the action of the depleting torsion spring 90.

Between the two ratchet features 222, 224 there is provided a rather plane shaped intermediate section 223, 225 that is void of protrusions or recesses. When a counter ratchet feature 242, 244 is in engagement with an intermediate section 223, 225 of the ratchet surface 221 the ratchet mechanism only provides a rather small resistance against the action of the depleting torsion spring 90. Here, the ratchet member 220 can be rotated relative to the counter ratchet member 240 along the first sense of rotation 5 if a torque equal to or above a predefined second torque M2 is present between the ratchet member 220 and the counter ratchet member 240.

The magnitude of the second torque M2 may even be equal to zero or may be almost equal to zero. As long as each one of the ratchet features and counter ratchet features of one of the ratchet surface and the counter ratchet surface is exclusively engaged with an intermediate section of the other one of the ratchet surface and the counter ratchet surface the ratchet member can be rotated along the first sense of rotation 5 under the action of the depleting torsion spring 90 until at least one of the ratchet features 222, 224 engages with at least one of the counter ratchet features 242, 244.

As indicated in FIGS. 24 and 25 the angular or circumferential size of the intermediate sections 223, 225, 243, 245 is larger, even much larger, than the circumferential extension of the ratchet features 222, 224 and the counter ratchet features 242, 244.

In the example as illustrated in FIGS. 24 and 25 the two ratchet features 222, 224 of the ratchet surface 221 are equidistantly spaced on the ratchet surface 221. The counter ratchet features 242, 244 are also equally or equidistantly spaced on the counter ratchet surface 241. With two equidistantly spaced ratchet features and counter ratchet features on each of the ratchet surface 221 and the counter ratchet surface 241 there are provided two pairs of mutually engaging ratchet features 222, 224 and counter ratchet features 242, 244. A holding torque or stop torque to be transferred between the ratchet member 220 and the counter ratchet member 240 can thus be split among the pairs of inter-engaging ratchet features 222, 224 and counter ratchet features 242, 244.

In this way, the robustness of the ratchet mechanism 200 can be increased and a susceptibility of the ratchet features 222, 224 and the counter ratchet features 242, 244 against mechanical damage or breakage can be reduced.

Figure 26:
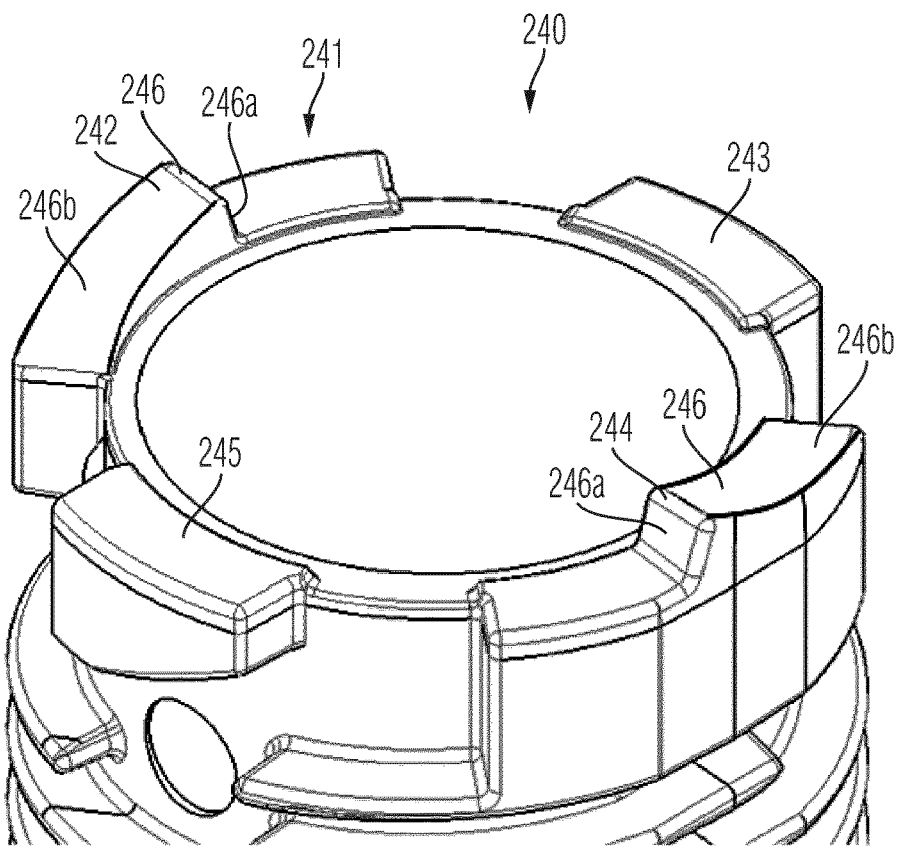
FIG. 26 is an enlarged view of the counter ratchet surface of the counter ratchet member, FIG. 27 schematically illustrates the mutual engagement of at least one ratchet feature with at least one counter ratchet feature.

As illustrated further in FIGS. 26 and 27 the circumferential extension of the second ramped section 226b, 246b compared to the circumferential extension of the first ramped section 226a, 246a is comparatively large. In this way the ramp angle of the second ramped section 226b, 246b is substantially smaller than the ramp angle of the first ramped section 226a, 246a. In one aspect this provides a rather smooth and easy rotation of the ratchet member 220 relative to the counter ratchet member 240 along the second sense of rotation 6. Here, the comparatively shallow ramp angles of the second ramped sections 226b, 246b only provide a comparatively low mechanical resistance. In another aspect the comparatively large circumferential extension of the second ramped sections 226b, 246b increases the mechanical stability of the teeth 226, 246 of the ratchet features 222, 224 and the counter ratchet features 242, 244.

Especially when the ratchet member 220 should be subject to a spring-driven rotation along the first sense of rotation 5 it may engage with its first ramped section 226a with a correspondingly shaped first ramped section 246a at a comparatively large angular velocity. The comparatively large circumferential extension of the second ramped sections 226b, 246b increases the mechanical rigidity and stability of the respective teeth specifically when the comparatively steep first ramped sections 226a, 246a mutually engage or mutually abut in circumferential or tangential direction.

Figure 28:
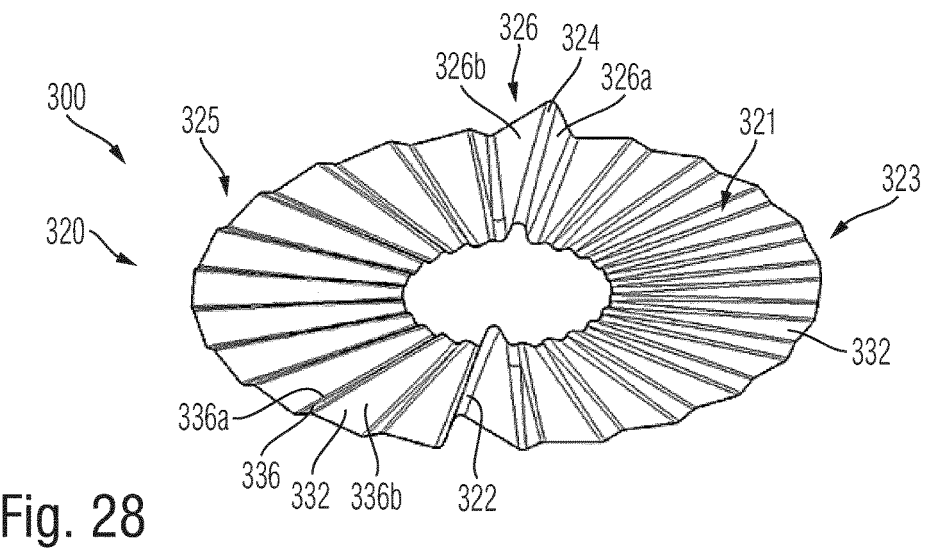
FIG. 28 shows another example of a ratchet surface of a ratchet member.
Figure 29:
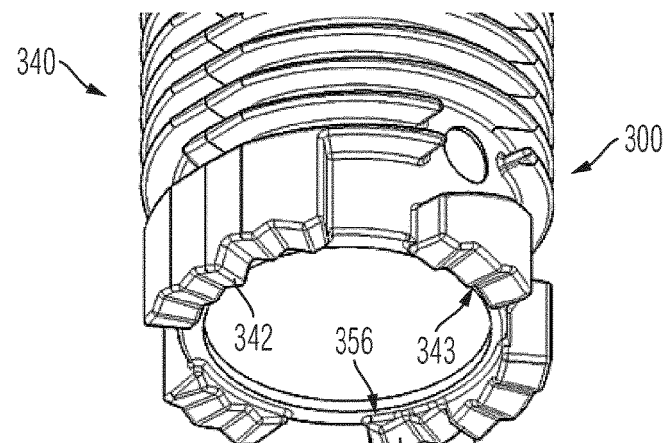
FIG. 29 shows another example of a counter ratchet surface of a counter ratchet member.
Figure 30:
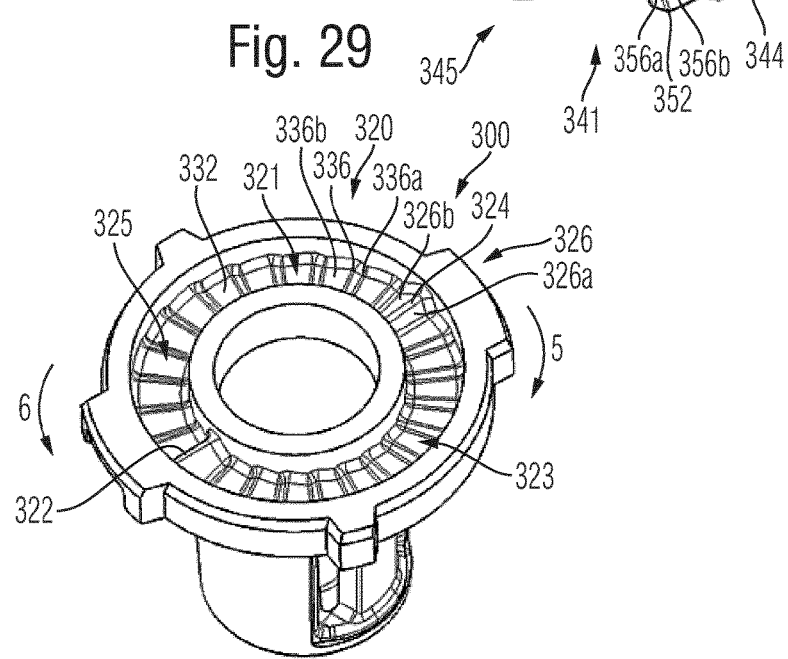
FIG. 30 shows the ratchet surface of FIG. 28 implemented in or on a ratchet member.

A further example of a ratchet mechanism 300 in accordance to the FIGS. 28-30 is substantially equivalent to the ratchet mechanism 200 as described above in connection with FIGS. 23-27. Here and contrary to ratchet mechanism 200 the intermediate sections 323, 325, 342, 344, located between the ratchet features 322, 324 and the counter ratchet features 343, 345, are not plane shaped, but comprise at least one or numerous intermediate ratchet features 332, 352. Also here the ratchet surface 321 of the ratchet member 320 comprises two ratchet features 322, 324 each comprising a ratchet tooth 326 with a first ramped section 326a and a second ramped section 326b.

In general the description and the features described in context with the FIGS. 23-27 equally apply to the example of FIGS. 28-30 unless mentioned otherwise. Components or features of the ratchet mechanism 200 equally apply to components and features of the ratchet mechanism 300. Components and features of the ratchet mechanism 200 and the ratchet mechanism 300 are identified by the same reference numbers, wherein the reference numbers of the ratchet mechanism 300 are increased by 100 compared to components and features of the ratchet mechanism 200.

The counter ratchet surface 341 comprises two substantially identically shaped counter ratchet features 342, 344 each comprising a counter ratchet tooth 346 having a first ramped section 346a and a second ramped section 346b. The ratchet features 322, 324 are equidistantly arranged along the circumference of the annular-shaped ratchet surface 321.

The intermediate sections 323, 325 located between the two ratchet features 322, 324 comprise numerous intermediate ratchet features 332. Each one of the intermediate ratchet features 332 comprises an intermediate ratchet tooth 336 having a first ramped section 336a and a second ramped section 336b. The first and the second ramped sections 336a, 336b are located at opposite side edges of the intermediate ratchet tooth 336.

The longitudinal or axial height of the intermediate teeth 336 is smaller than a height of the ratchet teeth 326. In this way and when a counter ratchet feature 342, 344 is out of engagement from any of the ratchet features 322, 324 and is in engagement with at least one intermediate ratchet member 332 the ratchet member 320 can be rotated along the first sense of rotation 5 as soon as a torque above a third torque M3 is applied between the ratchet member 320 and the counter ratchet member 340. Typically, this third torque M3 is smaller than a driving torque provided by the torsion spring 90. The mutual engagement of the intermediate ratchet features 332 with a counter ratchet feature 342, 344 provides a braking effect to the torsion spring induced rotation of the ratchet member 320 along the first sense of rotation 5. This engagement further provides an audible and/or haptic feedback to the user as a dose is set, e.g. when the ratchet member 320 is subject to a rotation relative to the counter ratchet member 340 along the second sense of rotation.

It is generally sufficient, when at least one of the ratchet surface 321 and the counter ratchet surface 341 is provided with at least one or numerous intermediate ratchet features 332, 352. In the example as illustrated in the FIGS. 28-30 both, the ratchet surface 321 and the counter ratchet surface 341 are provided with numerous equidistantly and regularly arranged intermediate ratchet features 332, 352. The intermediate ratchet features 352 may be identically shaped or may correspond to the intermediate ratchet member 332. The intermediate ratchet features 352 may each comprise an intermediate ratchet tooth 356 having a first ramped section 356a and a second ramped section 356b. Also here, the axial or longitudinal extension or height of the intermediate ratchet teeth 356 is smaller than the axial or longitudinal extension or height of the counter ratchet features 342, 344.

In other examples currently not illustrated it is also conceivable to modify the ramp angles of the first and/or second ramped sections 326a, 356a, 326b, 356b compared to the ramp angles of first and second ramped sections 326a, 346a, 326b, 346b so as to provide a holding torque M3 that is less than the first torque M1. Generally, at least one of the ramp angles and the longitudinal extension or height of the intermediate ratchet features varies from the respective ramp angles and/or longitudinal extension or height of the ratchet features or counter ratchet features.

The total number of intermediate ratchet features 332 and ratchet features 322, 324 may be equal to the number of ratchet features or clicker features of other ratchet mechanisms or clicker mechanisms provided in the injection device. The angular or circumferential width of the intermediate ratchet features 332 and the ratchet features 322, 324 may be substantially identical. A full revolution of the ratchet member 320 may be thus divided into a number of discrete steps of equal step size. The granularity or the step size, hence the total number of intermediate ratchet features 332 and ratchet features 322, 324 may be equal to the number of splines 66 of the dose indicator 60 or may be equal to the number of splines or ratchet teeth 75 of the button 70.

The above given description regarding the total number of intermediate ratchet features 332 and ratchet features 322, 324 may equally apply to the counter ratchet member 340.

REFERENCE NUMERALS

1 injection device
2 distal direction
3 proximal direction
5 first sense of rotation
6 second sense of rotation
10 housing
11a, b opening
12 flange-like inner wall
13 strip
14 teeth
15 spline
16 inner thread
20 cartridge holder
30 lead screw (piston rod)
31 outer thread
32 clip arm
33 concave contact surface
40 driver (axially movable drive sleeve)
41 teeth
42 spline
43 ratchet teeth
44 threaded section
45 spline
46 last dose stop
47 ramp
50 nut
51 last dose stop
52 spline
60 dose indicator (number sleeve)
60a number sleeve lower
60b number sleeve upper
61 spline
62 flange
63 outer thread
64, 65 end stop
66 spline
67 clicker arm
68 groove
69 anchor point
70 button
71 stem
72 flange
73, 74 spline
75 ratchet teeth
80 dose selector
90 torsion spring
91, 92 hook
93, 94 coil
100 cartridge
101 bung
110 gauge element
111 helical feature
112, 113 stop
114 aperture
115, 116 flange
117 cam
118 recess
120 clutch plate
121 ratchet teeth
122 protrusion
123 clicker arm
130 clutch spring
140 bearing
141 disc
142 stem
143 convex contact surface
144 recessed portion
200 ratchet mechanism
220 ratchet member
221 ratchet surface
222 ratchet feature
223 intermediate section
224 ratchet feature
225 intermediate section
226 tooth
226a, b ramped section
230 annular groove
231 stem section
232 flange section
233 protrusion
240 counter ratchet member
241 counter ratchet surface
242 counter ratchet feature
243 intermediate section
244 counter ratchet feature
245 intermediate section
246 tooth
246a, b ramped section
300 ratchet mechanism
320 ratchet member
321 ratchet surface
322 ratchet feature
323 intermediate section
324 ratchet feature
325 intermediate section
326 tooth
326a, b ramped section
332 intermediate ratchet member
336 tooth
336a, b ramped section
340 counter ratchet member
341 counter ratchet surface
342 counter ratchet feature
343 intermediate section
344 counter ratchet feature
345 intermediate section
346 tooth
346a, b ramped section
352 intermediate ratchet feature
356 tooth
356a, b ramped section

The invention claimed is:

1. A ratchet mechanism configured for an injection device, the ratchet mechanism comprising:
a housing;
a ratchet member that is circularly shaped and rotationally supported relative to the housing, the ratchet member comprising:
a ratchet surface,
a plurality of ratchet features on the ratchet surface, and
one or more intermediate ratchet sections on the ratchet surface extending between the plurality of ratchet features; and
a counter ratchet member that is circularly shaped, coaxially arranged relative to the ratchet member, rotatable relative to the ratchet member at least along a first sense of rotation, and rotationally supported relative to the housing, the counter ratchet member comprising:

a counter ratchet surface,
a plurality of counter ratchet features on the counter ratchet surface, and
one or more intermediate counter ratchet sections on the counter ratchet surface extending between the plurality of counter ratchet features,
wherein rotation of the ratchet member relative to the counter ratchet member along the first sense of rotation comprises:
application of at least a first torque between the ratchet member and the counter ratchet member when at least one of the plurality of ratchet features is in engagement with at least one of the plurality of counter ratchet features, and
application of at least a second torque that is smaller than the first torque between the ratchet member and the counter ratchet member when each of the plurality of ratchet features is out of engagement with any of the plurality of counter ratchet features.

2. The ratchet mechanism according to claim 1, wherein the ratchet member comprises two or more ratchet features equidistantly spaced on the ratchet surface.

3. The ratchet mechanism according to claim 1, wherein the counter ratchet member comprises two or more counter ratchet features equidistantly spaced on the counter ratchet surface.

4. The ratchet mechanism according to claim 1, wherein a number of ratchet features on the ratchet surface equals a number of counter ratchet features on the counter ratchet surface.

5. The ratchet mechanism according to claim 1, wherein a number of ratchet features on the ratchet surface is larger or smaller than a number of counter ratchet features on the counter ratchet surface.

6. The ratchet mechanism according to claim 1, wherein at least one of the plurality of ratchet features and the plurality of counter ratchet features comprises a tooth protruding from the ratchet surface or from the counter ratchet surface, wherein the tooth comprises a first ramped section and a second ramped section opposite to the first ramped section, wherein a first ramp angle of the first ramped section differs from a second ramp angle of the second ramped section.

7. The ratchet mechanism according to claim 6, wherein the at least one of the plurality of ratchet features comprises a tooth protruding from the ratchet surface, and wherein a respective counter ratchet feature comprises a tooth protruding from the counter ratchet surface.

8. The ratchet mechanism according to claim 6, wherein the first ramp angle of the first ramped section is larger than the second ramp angle of the second ramped section.

9. The ratchet mechanism according to claim 6, wherein a second circumferential extension of the second ramped section is at least two times or three times larger than a first circumferential extension of the first ramped section.

10. The ratchet mechanism according to claim 1, wherein intermediate sections of at least one of the ratchet surface and the counter ratchet surface are planar shaped and void of protrusions or recesses.

11. The ratchet mechanism according to claim 1, wherein at least one of the ratchet surface and the counter ratchet surface comprises at least one intermediate ratchet feature, wherein rotation of the ratchet member relative to the counter ratchet member along the first sense of rotation comprises application of at least a third torque between the ratchet member and the counter ratchet member along the first sense of rotation when the at least one intermediate ratchet feature is in engagement with at least one ratchet feature or counter ratchet feature, wherein the third torque is larger than the second torque, and wherein the third torque is smaller than the first torque.

12. The ratchet mechanism according to claim 11, wherein a height of the at least one intermediate ratchet feature is smaller than a height of at least one of the plurality of ratchet features and is smaller than a height of at least one of the plurality of counter ratchet features.

13. The ratchet mechanism according to claim 11, wherein the at least one intermediate ratchet feature comprises a tooth protruding from an intermediate section, wherein the tooth comprises a first ramped section and a second ramped section opposite to the first ramped section, and wherein a ramp angle of the first ramped section of the at least one intermediate ratchet feature is smaller than a ramp angle of a first ramped section of a tooth of at least one of the ratchet feature or counter ratchet feature.

14. The ratchet mechanism according to claim 1, wherein at least one of the ratchet surface and the counter ratchet surface comprises at least one intermediate ratchet feature, wherein rotation of the ratchet member relative to the counter ratchet member along the first sense of rotation comprises application of at least a third torque between the ratchet member and the counter ratchet member along the first sense of rotation when the at least one intermediate ratchet feature is in engagement with at least one ratchet feature or counter ratchet feature, wherein the third torque is larger than the second torque, wherein the third torque is smaller than the first torque, and wherein the ratchet member is rotatable along a second sense of rotation against an action of a torsion spring, wherein the torsion spring is configured to apply a driving torque to the ratchet member, wherein the driving torque is smaller than the first torque, and wherein the driving torque is larger than the second torque.

15. The ratchet mechanism according to claim 14, wherein the driving torque is larger than the third torque.

16. An injection device for expelling of a number of preset or user-selectable doses of a medicament, the injection device comprising:
an elongated housing extending along a longitudinal axis, the elongated housing being configured to accommodate a cartridge containing the medicament and having a bung sealing a proximal end of the cartridge;
a piston rod configured to urge against the bung along the longitudinal axis in a distal direction relative to the elongated housing;
a dose selector rotatable relative to the elongated housing for setting of a dose; and
a ratchet mechanism comprising:
a housing,
a ratchet member that is circularly shaped and rotationally supported relative to the housing, the ratchet member comprising:
a ratchet surface,
a plurality of ratchet features on the ratchet surface, and
one or more intermediate ratchet sections on the ratchet surface extending between the plurality of ratchet features, and
a counter ratchet member that is circularly shaped, coaxially arranged relative to the ratchet member, rotatable relative to the ratchet member at least along a first sense of rotation, and rotationally supported relative to the housing, the counter ratchet member comprising:
a counter ratchet surface, a plurality of counter ratchet features on the counter ratchet surface, and
one or more intermediate counter ratchet sections on the counter ratchet surface extending between the plurality of counter ratchet features,
wherein rotation of the ratchet member relative to the counter ratchet member along the first sense of rotation comprises:
application of at least a first torque between the ratchet member and the counter ratchet member when at least one of the plurality of ratchet features is in engagement with at least one of the plurality of counter ratchet features, and
application of at least a second torque that is smaller than the first torque between the ratchet member and the counter ratchet member when each of the plurality of ratchet features is out of engagement with any of the plurality of counter ratchet features, and
wherein the ratchet member is rotationally locked to the dose selector at least during setting of the dose, and wherein the counter ratchet member is rotationally engageable or rotationally lockable with at least one of the piston rod and the elongated housing at least for expelling of the dose.

17. The injection device according to claim 16, wherein the counter ratchet member is rotatable relative to the elongated housing at least during expelling of the dose and for urging the piston rod against the bung.

18. The injection device according to claim 16, wherein the ratchet member comprises two or more ratchet features equidistantly spaced on the ratchet surface.

19. The injection device according to claim 16, wherein the counter ratchet member comprises two or more counter ratchet features equidistantly spaced on the counter ratchet surface.

20. The injection device according to claim 16, further comprising the cartridge containing the medicament within the elongated housing.

* * * * *